(12) United States Patent
Albrecht et al.

(10) Patent No.: US 11,510,695 B2
(45) Date of Patent: Nov. 29, 2022

(54) MULTIFUNCTIONAL SURGICAL ACCESS SYSTEM

(71) Applicant: Applied Medical Resources Corporation, Rancho Santa Margarita, CA (US)

(72) Inventors: Jeremy J. Albrecht, Rancho Santa Margarita, CA (US); Eric Nguyen, Rancho Santa Margarita, CA (US); Matthew M. Becerra, Lake Forest, CA (US); Gary M. Johnson, Rancho Santa Margarita, CA (US); John R. Brustad, Rancho Santa Margarita, CA (US); Ghassan Sakakine, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 379 days.

(21) Appl. No.: 16/455,525

(22) Filed: Jun. 27, 2019

(65) Prior Publication Data
US 2020/0085467 A1     Mar. 19, 2020

Related U.S. Application Data

(63) Continuation of application No. 15/658,248, filed on Jul. 24, 2017, now abandoned, which is a
(Continued)

(51) Int. Cl.
*A61B 17/02* (2006.01)
*A61B 17/34* (2006.01)
*A61B 90/00* (2016.01)

(52) U.S. Cl.
CPC ...... *A61B 17/3423* (2013.01); *A61B 17/0218* (2013.01); *A61B 17/3496* (2013.01);
(Continued)

(58) Field of Classification Search
CPC .............................................. Y10T 403/7045
See application file for complete search history.

(56) References Cited

U.S. PATENT DOCUMENTS

| 558,364 A | 4/1896 | Doolittle |
|---|---|---|
| 1,157,202 A | 10/1915 | Bates et al. |

(Continued)

FOREIGN PATENT DOCUMENTS

| DE | 19828009 | 12/1999 |
|---|---|---|
| EP | 1 125 552 | 8/2001 |

(Continued)

OTHER PUBLICATIONS

European Patent Office, Extended European Search Report for European Patent Application No. EP 19213801, titled "Multifunctional Surgical Access System," dated Mar. 3, 2020, 10 pgs.
(Continued)

*Primary Examiner* — Jan Christopher L Merene
(74) *Attorney, Agent, or Firm* — Thomas Nguyen; Patrick Ikehara

(57) ABSTRACT

A tissue retractor comprising an outer ring, an inner ring, and a flexible, metal sheath extending therebetween is described. Embodiments of the inner ring comprise a flat or wedge-shaped conformation useful for insertion between muscle layers. Other embodiments of the inner ring include variable diameter inner rings, where the diameter can be adjusted as required and optionally locked into place, and reshapeable inner rings that permit a user to conform the inner ring to the anatomy of the patient when placing the inner ring.

9 Claims, 12 Drawing Sheets

Related U.S. Application Data continuation of application No. 14/794,400, filed on Jul. 8, 2015, now Pat. No. 9,743,954, which is a continuation of application No. 12/873,115, filed on Aug. 31, 2010, now Pat. No. 9,717,522.

(60) Provisional application No. 61/238,540, filed on Aug. 31, 2009.

(52) U.S. Cl.
 CPC ....... *A61B 17/3431* (2013.01); *A61B 17/3494* (2013.01); *A61B 2090/0801* (2016.02)

(56) References Cited

U.S. PATENT DOCUMENTS

| | | |
|---|---|---|
| 1,810,466 A | 6/1931 | Deutsch |
| 2,305,289 A | 12/1942 | Coburg |
| 2,478,586 A | 8/1949 | Krapp |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,111,943 A | 11/1963 | Orndorff |
| 3,195,934 A | 7/1965 | Parrish |
| 3,244,169 A | 4/1966 | Baxter |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,523,534 A | 8/1970 | Nolan |
| 3,660,869 A | 5/1972 | Caveney et al. |
| 3,717,151 A | 2/1973 | Collett |
| 3,744,489 A * | 7/1973 | Munro .................... A61F 6/142 128/839 |
| 3,799,152 A * | 3/1974 | Kim ...................... A61B 1/2733 600/139 |
| 3,831,583 A | 8/1974 | Edmunds et al. |
| 3,841,332 A | 10/1974 | Treacle |
| 3,850,172 A | 11/1974 | Cazalis |
| 3,856,021 A | 12/1974 | McIntosh |
| 3,860,274 A | 1/1975 | Ledstrom et al. |
| 4,024,872 A | 5/1977 | Muldoon |
| 4,043,328 A | 8/1977 | Cawood, Jr. et al. |
| 4,069,913 A | 1/1978 | Harrigan |
| 4,083,370 A | 4/1978 | Taylor |
| 4,188,945 A | 2/1980 | Wenander |
| 4,217,664 A | 8/1980 | Faso |
| 4,222,126 A | 9/1980 | Boretos et al. |
| 4,254,973 A | 3/1981 | Benjamin |
| 4,261,352 A * | 4/1981 | Sedlacek .................. A61F 6/08 128/837 |
| 4,338,937 A | 7/1982 | Leman |
| 4,367,728 A | 1/1983 | Mutke |
| 4,369,284 A | 1/1983 | Chen |
| 4,454,873 A | 6/1984 | Lautenberg et al. |
| 4,475,548 A | 10/1984 | Muto |
| 4,550,713 A | 11/1985 | Hyman |
| 4,553,537 A | 11/1985 | Rosenberg |
| 4,691,942 A | 9/1987 | Ford |
| 4,714,749 A | 12/1987 | Hughes et al. |
| 4,755,170 A | 7/1988 | Golden |
| 4,776,067 A | 10/1988 | Sorensen |
| 4,777,943 A | 10/1988 | Chvapil |
| 4,798,594 A | 1/1989 | Hillstead |
| 4,802,694 A | 2/1989 | Vargo |
| 4,842,931 A | 6/1989 | Zook |
| 4,856,502 A | 8/1989 | Ersfeld et al. |
| 4,863,438 A | 9/1989 | Gauderer et al. |
| 4,889,107 A | 12/1989 | Kaufman |
| 4,895,565 A | 1/1990 | Hillstead |
| 4,901,372 A | 2/1990 | Pierce |
| 4,903,710 A | 2/1990 | Jessamine et al. |
| 4,911,974 A | 3/1990 | Shimizu et al. |
| 4,926,882 A | 5/1990 | Lawrence |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,037,379 A | 8/1991 | Clayman et al. |
| 5,082,005 A | 1/1992 | Kaldany |
| 5,156,233 A * | 10/1992 | Olsen ..................... E04G 17/00 182/3 |
| 5,159,921 A | 11/1992 | Hoover |
| 5,178,162 A | 1/1993 | Bose |
| 5,180,365 A | 1/1993 | Ensminger et al. |
| 5,192,301 A | 3/1993 | Kamiya et al. |
| 5,207,656 A | 5/1993 | Kranys |
| 5,213,114 A | 5/1993 | Bailey, Jr. |
| 5,259,366 A | 11/1993 | Reydel et al. |
| 5,262,468 A | 11/1993 | Chen |
| 5,299,582 A | 4/1994 | Potts |
| 5,316,541 A | 5/1994 | Fischer |
| 5,336,708 A | 8/1994 | Chen |
| 5,342,385 A | 8/1994 | Norelli et al. |
| 5,350,364 A | 9/1994 | Stephens et al. |
| 5,353,786 A | 10/1994 | Wilk |
| 5,366,478 A | 11/1994 | Brinkerhoff et al. |
| 5,368,545 A | 11/1994 | Schaller et al. |
| 5,380,288 A | 1/1995 | Hart et al. |
| 5,389,080 A | 2/1995 | Yoon |
| 5,389,081 A | 2/1995 | Castro |
| 5,407,433 A | 4/1995 | Loomas |
| 5,429,609 A | 7/1995 | Yoon |
| 5,437,683 A | 8/1995 | Neumann et al. |
| 5,441,486 A | 8/1995 | Yoon |
| 5,456,284 A | 10/1995 | Ryan et al. |
| 5,460,616 A | 10/1995 | Weinstein et al. |
| 5,476,475 A | 12/1995 | Gadberry |
| 5,480,410 A | 1/1996 | Cushieri et al. |
| 5,486,426 A | 1/1996 | McGee et al. |
| 5,492,304 A | 2/1996 | Smith et al. |
| 5,496,280 A | 3/1996 | Vandenbroek et al. |
| 5,503,112 A | 4/1996 | Luhman et al. |
| 5,508,334 A | 4/1996 | Chen |
| 5,514,133 A | 5/1996 | Goulb et al. |
| 5,518,278 A | 5/1996 | Sampson |
| 5,522,791 A | 6/1996 | Leyva |
| 5,524,644 A | 6/1996 | Crook |
| 5,531,758 A | 7/1996 | Uschold et al. |
| 5,545,179 A | 8/1996 | Williamson, IV |
| 5,562,677 A | 10/1996 | Hildwein et al. |
| 5,603,702 A | 2/1997 | Smith et al. |
| 5,628,732 A | 5/1997 | Antoon, Jr. et al. |
| 5,632,284 A | 5/1997 | Graether |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | De la Torre et al. |
| 5,672,168 A | 9/1997 | De la Torre et al. |
| 5,681,341 A | 10/1997 | Lunsford et al. |
| 5,709,664 A | 1/1998 | Vandenbroek et al. |
| 5,720,730 A | 2/1998 | Blake, III |
| 5,728,103 A | 3/1998 | Picha et al. |
| 5,741,298 A | 4/1998 | MacLeod |
| 5,760,117 A | 6/1998 | Chen |
| 5,782,817 A | 7/1998 | Franzel et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,810,721 A | 9/1998 | Mueller et al. |
| 5,813,409 A | 9/1998 | Leahy et al. |

(56) References Cited

U.S. PATENT DOCUMENTS

| | | |
|---|---|---|
| 5,814,026 A | 9/1998 | Yoon |
| 5,819,375 A | 10/1998 | Kastner |
| 5,832,925 A | 11/1998 | Rothrum |
| 5,841,298 A | 11/1998 | Huang |
| 5,853,395 A | 12/1998 | Crook et al. |
| 5,865,729 A | 2/1999 | Meehan et al. |
| 5,865,807 A | 2/1999 | Blake, III |
| 5,871,474 A | 2/1999 | Hermann et al. |
| 5,895,377 A | 4/1999 | Smith et al. |
| 5,899,208 A | 5/1999 | Bonadio |
| 5,904,703 A | 5/1999 | Gilson |
| 5,906,577 A | 5/1999 | Beane et al. |
| 5,911,392 A | 6/1999 | Greenslate |
| 5,919,476 A | 7/1999 | Fischer et al. |
| 5,947,922 A | 9/1999 | MacLeod |
| 5,951,588 A | 9/1999 | Moenning |
| 5,957,888 A | 9/1999 | Hinchiffe |
| 5,957,913 A | 9/1999 | De la Torre |
| 5,962,572 A | 10/1999 | Chen |
| 5,964,781 A | 10/1999 | Mollenauer et al. |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,997,515 A | 12/1999 | De la Torre et al. |
| 6,010,494 A | 1/2000 | Schafer et al. |
| D421,235 S * | 2/2000 | Rausch .................. D10/113.3 |
| 6,024,736 A | 2/2000 | De la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,045,535 A | 4/2000 | Be Nun |
| 6,053,934 A | 4/2000 | Andrews et al. |
| 6,077,288 A | 6/2000 | Shimomura |
| 6,090,043 A | 7/2000 | Austin et al. |
| 6,110,154 A | 8/2000 | Shimomura et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,162,172 A | 12/2000 | Cosgrove et al. |
| 6,224,612 B1 | 5/2001 | Bates et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,276,661 B1 | 8/2001 | Laird |
| 6,287,280 B1 | 9/2001 | Lampropoulos et al. |
| 6,319,246 B1 | 11/2001 | De la Torre |
| 6,325,384 B1 | 12/2001 | Berry, Sr. et al. |
| 6,382,211 B1 | 5/2002 | Crook |
| 6,383,162 B1 | 5/2002 | Sugarbaker |
| 6,413,244 B1 | 7/2002 | Bestetti et al. |
| 6,440,063 B1 | 8/2002 | Beane et al. |
| 6,450,983 B1 | 9/2002 | Rambo |
| 6,482,181 B1 | 11/2002 | Racenet et al. |
| 6,485,435 B1 | 11/2002 | Bakal |
| 6,533,734 B1 | 3/2003 | Corley, III et al. |
| 6,551,344 B2 | 4/2003 | Thill |
| 6,569,120 B1 | 5/2003 | Green et al. |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,613,952 B2 | 9/2003 | Rambo |
| 6,623,426 B2 | 9/2003 | Bonadio et al. |
| 6,663,598 B1 | 12/2003 | Carrillo, Jr. et al. |
| 6,702,787 B2 | 3/2004 | Racenet et al. |
| 6,723,044 B2 | 4/2004 | Pulford et al. |
| 6,814,078 B2 | 11/2004 | Crook |
| 6,846,287 B2 | 1/2005 | Bonadio et al. |
| 6,866,861 B1 | 3/2005 | Luhman |
| 6,895,965 B2 | 5/2005 | Scarberry et al. |
| 6,902,541 B2 | 6/2005 | McNally et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,997,909 B2 | 2/2006 | Goldberg |
| 7,033,319 B2 | 4/2006 | Pulford et al. |
| 7,052,454 B2 | 5/2006 | Taylor |
| 7,081,089 B2 | 7/2006 | Bonadio et al. |
| 7,214,185 B1 | 5/2007 | Rosney et al. |
| 7,235,062 B2 | 6/2007 | Brustad et al. |
| 7,311,719 B2 | 12/2007 | Bonutti |
| 7,704,207 B2 * | 4/2010 | Albrecht ............ A61B 17/3431 |
| | | 600/208 |
| 8,132,372 B2 * | 3/2012 | Mower .................. E04D 3/357 |
| | | 52/79.1 |
| 11,091,957 B2 * | 8/2021 | Voss ........................ E06C 1/10 |
| 2001/0004823 A1 * | 6/2001 | Cronin .................... E06C 7/187 |
| | | 52/651.01 |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0038077 A1 | 3/2002 | De la Torre et al. |
| 2002/0072762 A1 | 6/2002 | Bonadio et al. |
| 2002/0152707 A1 * | 10/2002 | Martensson .......... E04B 1/6129 |
| | | 52/592.2 |
| 2003/0040711 A1 | 2/2003 | Racenet et al. |
| 2003/0187376 A1 | 10/2003 | Rambo |
| 2003/0192553 A1 | 10/2003 | Rambo |
| 2003/0225392 A1 | 12/2003 | McMichael et al. |
| 2004/0015185 A1 | 1/2004 | Ewers et al. |
| 2004/0049009 A1 | 3/2004 | Ewers et al. |
| 2004/0049100 A1 | 3/2004 | Butler et al. |
| 2004/0054353 A1 * | 3/2004 | Taylor ................ A61B 17/3423 |
| | | 606/1 |
| 2004/0073090 A1 | 4/2004 | Butler et al. |
| 2004/0092796 A1 | 5/2004 | Butler et al. |
| 2004/0106942 A1 | 6/2004 | Taylor et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0254426 A1 | 12/2004 | Wenchell |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0090717 A1 | 4/2005 | Bonadio et al. |
| 2005/0148823 A1 | 7/2005 | Vaugh et al. |
| 2005/0155611 A1 | 7/2005 | Vaugh et al. |
| 2005/0192482 A1 | 9/2005 | Carpenter |
| 2005/0197537 A1 | 9/2005 | Bonadio et al. |
| 2005/0222582 A1 | 10/2005 | Wenchell |
| 2005/0241647 A1 | 11/2005 | Nguyen et al. |
| 2005/0267419 A1 | 12/2005 | Smith |
| 2005/0283050 A1 | 12/2005 | Gundlapalli et al. |
| 2005/0288558 A1 | 12/2005 | Ewers et al. |
| 2006/0015136 A1 | 1/2006 | Besselink |
| 2006/0030755 A1 | 2/2006 | Ewers et al. |
| 2006/0047284 A1 | 3/2006 | Gresham |
| 2006/0052669 A1 | 3/2006 | Hart |
| 2006/0058790 A1 * | 3/2006 | Carl ...................... A61F 2/4405 |
| | | 606/248 |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2006/0247500 A1 | 11/2006 | Voegele et al. |
| 2007/0088204 A1 | 4/2007 | Albrecht et al. |
| 2009/0013721 A1 * | 1/2009 | Murao .................. A44C 5/2014 |
| | | 63/3.1 |
| 2009/0069627 A1 | 3/2009 | Haindl |
| 2010/0063452 A1 | 3/2010 | Edelman et al. |
| 2010/0081995 A1 | 4/2010 | Widenhouse et al. |

(56) References Cited

U.S. PATENT DOCUMENTS

| | | | | |
|---|---|---|---|---|
| 2010/0180762 A1* | 7/2010 | Raffaele | .................. | F01B 9/023 92/140 |
| 2010/0228090 A1 | 9/2010 | Weisenburgh et al. | | |
| 2015/0119647 A1* | 4/2015 | Vaillancourt | ...... | A61B 17/3423 600/208 |

FOREIGN PATENT DOCUMENTS

| | | |
|---|---|---|
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 11-290327 | 10/1999 |
| JP | 2002-28163 | 1/2002 |
| JP | 02003 235879 A | 8/2003 |
| WO | WO 91/02466 | 3/1991 |
| WO | WO95/07056 | 3/1995 |
| WO | WO95/22289 | 8/1995 |
| WO | WO95/24864 | 9/1995 |
| WO | WO95/27468 | 10/1995 |
| WO | WO97/11642 | 4/1997 |
| WO | WO98/19853 | 5/1998 |
| WO | WO98/35614 | 8/1998 |
| WO | WO98/48724 | 11/1998 |
| WO | WO99/15068 | 4/1999 |
| WO | WO99/25268 | 5/1999 |
| WO | WO00/32116 | 6/2000 |
| WO | WO00/32120 | 6/2000 |
| WO | WO00/35356 | 6/2000 |
| WO | WO00/54675 | 9/2000 |
| WO | WO00/54676 | 9/2000 |
| WO | WO00/54677 | 9/2000 |
| WO | WO01/08581 | 2/2001 |
| WO | WO01/26559 | 4/2001 |
| WO | WO02/34108 | 5/2002 |
| WO | WO03/032819 | 4/2003 |
| WO | WO03/034908 | 5/2003 |
| WO | WO03/061480 | 7/2003 |
| WO | WO03/077726 | 9/2003 |
| WO | WO03/103548 | 12/2003 |
| WO | WO2004/075730 | 9/2004 |
| WO | WO2004/075741 | 9/2004 |
| WO | WO2004/075930 | 9/2004 |
| WO | WO 2005/034766 | 4/2005 |
| WO | WO 2007/083305 | 7/2007 |
| WO | WO 2008/147644 | 12/2008 |

OTHER PUBLICATIONS

Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Dexterity Protractor Instruction Manual by Dexterity Surgical, Inc.
Horigane, et al., Technical Note: Development of a Duodoenal Cannula for Sheep, Journal of Animal Science, Apr. 1992, vol. 70, Issue 4, pp. 1216-1219.
Horigane, et al., Silicone Rumen Cannula with a Soft Cylindrical Part and a Hard Flange, Journal of Dairy Science, Nov. 1989, vol. 72, No. 11, pp. 3230-3232.
McSweeney, Cannulation of the Rumen in Cattle and Buffaloes, Australian Veterinary Journal, Aug. 1989, vol. 66, No. 8, pp. 266-268.
Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.
International Searching Authority/US, International Search Report and The Written Opinion of the International Searching Authority for International Application No. PCT/US04/05484, dated Nov. 12, 2004.
International Searching Authority/US, International Search Report and The Written Opinion of the International Searching Authority for International Application No. PCT/US01/29682, dated Jun. 14, 2002.
European Patent Office, International Search Report and The Written Opinion of the International Searching Authority for International Application No. PCT/US2006/040154, dated Jan. 30, 2007.
European Patent Office, International Search Report and The Written Opinion of the International Searching Authority for International Application No. PCT/2006/039799 dated Mar. 27, 2007.
The International Bureau of WIPO, International Preliminary Report on Patentability, dated Aug. 29, 2006, for international application No. PCT/US2004/028250.
The International Bureau of WIPO, International Preliminary Report on Patentability dated Apr. 16, 2008 for PCT Application No. PCT/US2006/039799 mailed Mar. 27, 2007.
European Patent Office, International Search Report and The Written Opinion of the International Searching Authority for International Application No. PCT/2006/040073 dated Jan. 26, 2007.
European Patent Office, International Search Report and The Written Opinion of the International Searching Authority for International Application No. PCT/2006/039905 dated Jan. 17, 2007.
European Patent Office, International Search Report and The Written Opinion of the International Searching Authority for International Application No. PCT/2006/039883, dated Jan. 31, 2007.
European Patent Office, International Search Report and The Written Opinion of the International Searching Authority for International Application No. PCT/2006/039800, dated Apr. 16, 2007.
European Patent Office, International Search Report and Written Opinion for International Application No. PCT/US2010/047368, dated Nov. 2, 2010, entitled Multi-Functional Surgical Access System.
The International Bureau of WIPO, International Preliminary Report on Patentability, for International Application No. PCT/US2010/047368, dated Mar. 6, 2012, entitled Multi-Functional Surgical Access System.
Co-Pending U.S. Appl. No. 10/381,220; filed Mar. 20, 2003; Title: Surgical Access Apparatus and Method.
Co-Pending U.S. Appl. No. 10/516,198; filed Nov. 30, 2004; Title: Wound Retractor.
Co-Pending U.S. Appl. No. 10/927,551; filed Aug. 25, 2004; Title: Surgical Access System.
Co-Pending U.S. Appl. No. 11/244,647; filed Oct. 5, 2005; Title: Surgical Access Apparatus and Method.
Co-Pending U.S. Appl. No. 11/245,709; filed Oct. 7, 2005; Title: Surgical Access System.
Co-Pending U.S. Appl. No. 11/330,661; filed Jan. 12, 2006; Title: Sealed Surgical Access Device.
Co-Pending U.S. Appl. No. 11/548,746; filed Oct. 12, 2006; Title: Method of Making a Hand Access Laparoscopic Device.
Co-Pending U.S. Appl. No. 11/548,758; filed Oct. 12, 2006; Title: Split Hoop Wound Retractor With Gel Pad.
Co-Pending U.S. Appl. No. 11/548,765; filed Oct. 12, 2006; Title: Split Hoop Wound Retractor.
Co-Pending U.S. Appl. No. 11/548,767; filed Oct. 12, 2006; Title: Circular Surgical Retractor.
Co-Pending U.S. Appl. No. 11/548,781; filed Oct. 12, 2006; Title: Wound Retractor With Gel Cap.
Co-Pending U.S. Appl. No. 11/548,955; filed Oct. 12, 2006; Title: Hand Access Laparoscopic Device.
Co-Pending U.S. Appl. No. 11/564,409; filed Nov. 29, 2006; Title: Surgical Instrument Access Device.

(56) References Cited

OTHER PUBLICATIONS

Co-Pending U.S. Appl. No. 11/755,305; filed May 30, 2007; Title: Wound Retraction Apparatus and Method.
Co-Pending U.S. Appl. No. 12/108,400, filed Apr. 23, 2008; Title: Wound Retraction Apparatus and Method.
Co-Pending U.S. Appl. No. 12/358,080, filed Jan. 22, 2009; Title: Surgical Instrument Access Device.

* cited by examiner

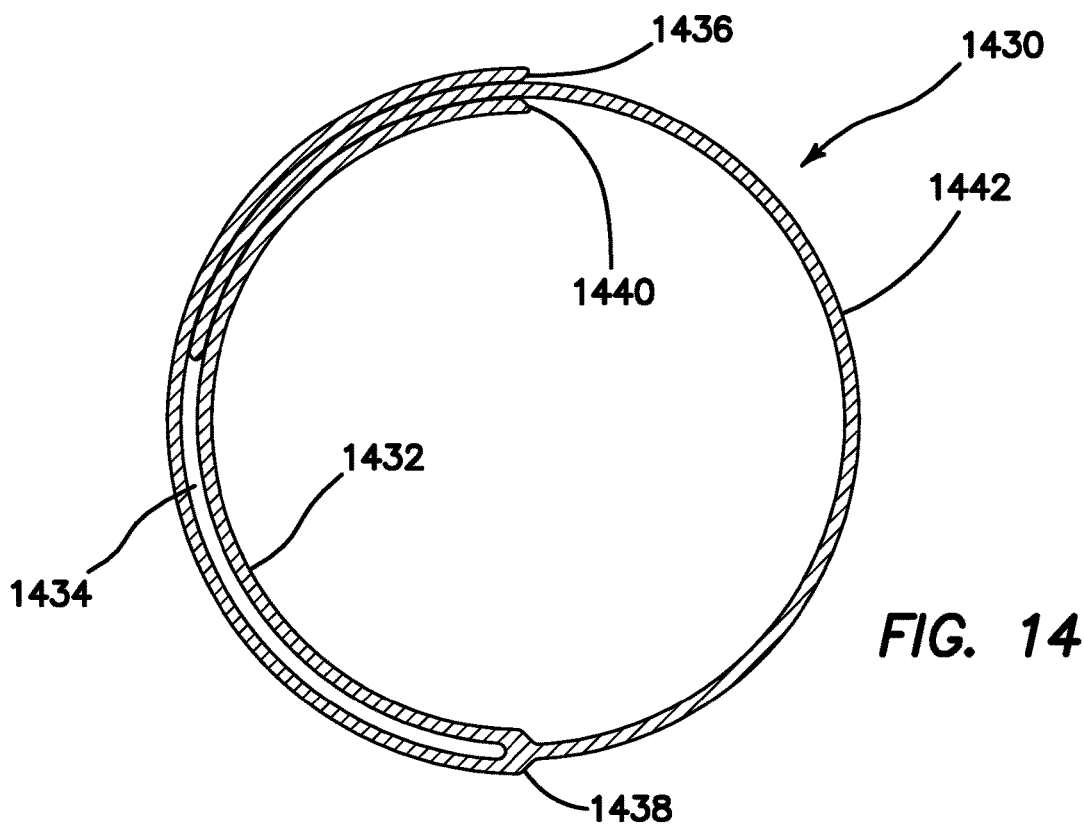
FIG. 14
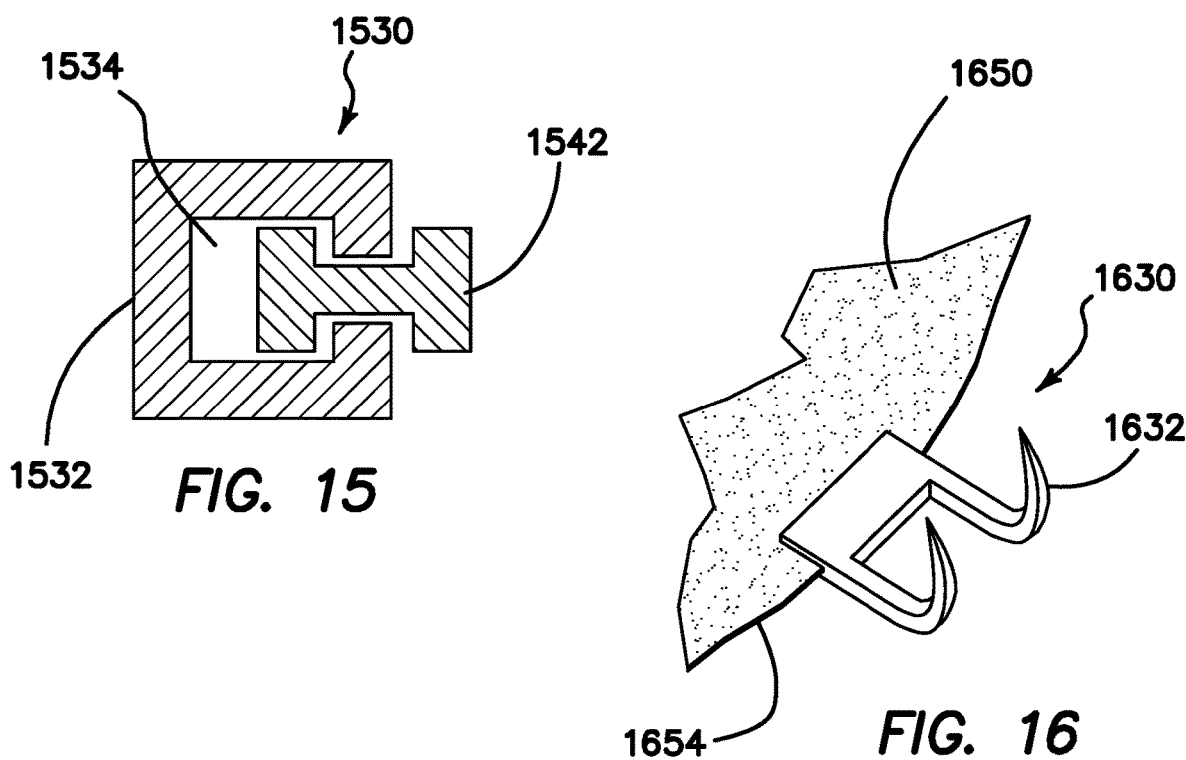
FIG. 15
FIG. 16

MULTIFUNCTIONAL SURGICAL ACCESS SYSTEM

CROSS REFERENCE TO RELATED APPLICATIONS

This application is a continuation of U.S. patent application Ser. No. 15/658,248, filed Jul. 24, 2017, which is a continuation of U.S. patent application Ser. No. 14/794,400, filed Jul. 8, 2015, now U.S. Pat. No. 9,743,954, which is a continuation of U.S. application Ser. No. 12/873,115, filed Aug. 31, 2010, now U.S. Pat. No. 9,717,522, which claims the benefit of U.S. Patent Application No. 61/238,540, filed Aug. 31, 2009, the entire disclosures of which are incorporated by reference.

BACKGROUND

Technical Field

This application is generally related to medical devices, and more particularly, to surgical access systems that include wound retractors.

Description of the Related Art

Wound retractors are used to expand or retract a surgical incision or natural orifice. Some wound retractors comprise a polymer film sheath disposed between an inner and outer ring. In use, the inner ring is inserted into a body cavity, such as an abdominal cavity, and the film is anchored to the outer ring under tension. The tensioned film stretches the incision or orifice, thereby improving access to the cavity. The polymer film sheath also lines the incision or opening, thereby protecting the soft tissue from contamination and/or physical damage.

SUMMARY OF THE INVENTION

A tissue retractor comprising a longitudinal axis defining an instrument access channel extending from a proximal end to a distal end, an outer ring, an inner ring, and a flexible sheath extending between the outer ring and the inner ring, wherein the instrument access channel extends through the outer ring, the inner ring, and the sheath is described.

In some embodiments, at least a portion of the cross-section of the inner ring is flat. In other embodiments, the cross-section of the inner ring is flat at its outer circumference, while in other embodiments, the entire cross-section of the inner ring is flat. In still other embodiments, the thickness of the cross-section at the inner circumference of the inner ring is greater than the thickness of the cross-section at the outer circumference of the inner ring.

In one embodiment, the inner ring comprises a single piece. In another embodiment, the inner ring comprises a plurality of pieces.

In one embodiment, the diameter of the inner ring is adjustable. In one embodiment, the inner ring comprises an elongate tubular body defining a lumen and wherein the tubular body comprises a first end, a second end, an opening into the lumen at the first end and an elongate shaft extending from the second end, the shaft adapted to be received through the opening into the lumen. Optionally, the inner ring further comprises a locking means for locking the shaft in the lumen of the tubular body to thereby fix the diameter of the inner ring.

In another embodiment, the inner ring comprises an elongate C-shaped tubular body defining a channel and wherein the tubular body comprises a first end, a second end, and an elongate shaft extending from the second end, the shaft adapted to be received into the channel. Optionally, the inner ring further comprises a locking means for locking the shaft in the channel of the tubular body to thereby fix the diameter of the inner ring.

In still another embodiment, the inner ring is reshapeable and comprises a plurality of linked, alternating arcuate members and straight members disposed end-to-end, wherein each arcuate member is rotatable relative to an adjacent straight member around a longitudinal axis.

BRIEF DESCRIPTION OF THE DRAWINGS

FIG. 14 is a top cross section of an embodiment of a resizable inner ring.

FIG. 15 is a side cross section of another embodiment of a resizable inner ring.

FIG. 16 is a perspective view of an embodiment of an inner anchor.

Similar reference numbers refer to similar components.

DETAILED DESCRIPTION OF CERTAIN EMBODIMENTS

Surgical access systems similar to embodiments disclosed herein are disclosed in U.S. Patent Publication Nos. 2005/

0241647 A1, 2007/0185387 A1, 2007/0149859 A1, and 2007/0088202 A1 the disclosures of which are incorporated by reference in their entireties.

Figure 1A:
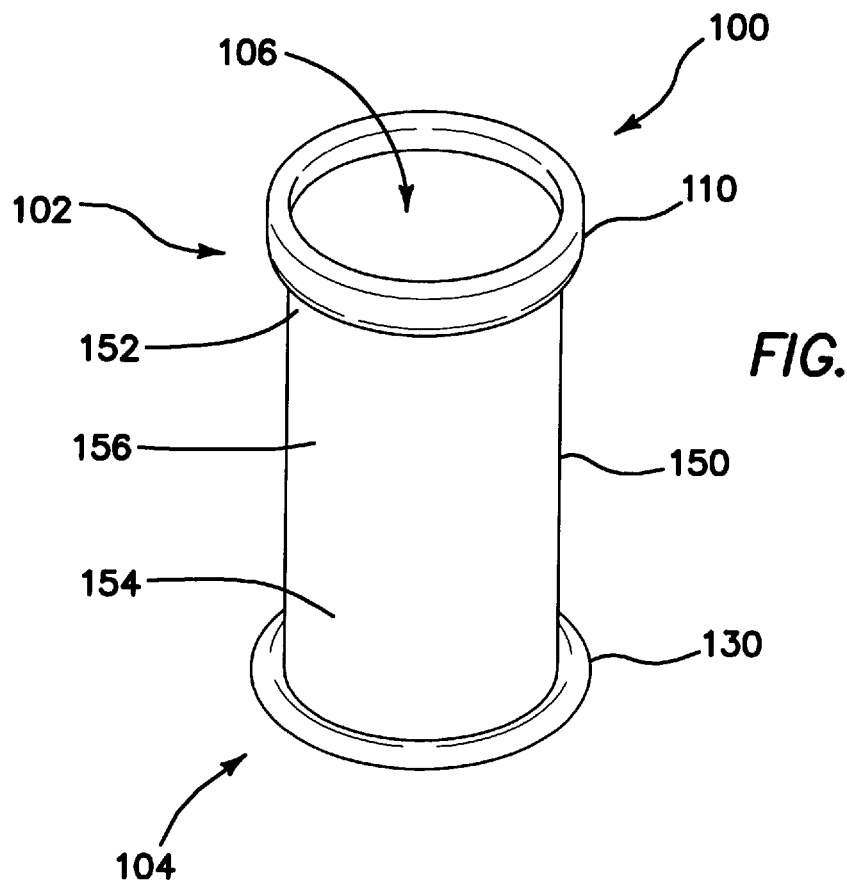
FIG. 1A is a perspective view of an embodiment of a retractor.

FIG. 1A is a perspective view of an embodiment of a wound retractor 100 of a surgical access system. The retractor 100 comprises a proximal end 102, a distal end 104, an instrument access channel 106, an outer or proximal anchor 110, and inner or distal anchor 130, and a flexible sheath 150 extending between the outer anchor 110 and the inner anchor 130. In the illustrated embodiment, both of the outer anchor 110 and the inner anchor 130 are ring-shaped, and consequently, are referred to as an outer ring 110 and an inner ring 130, respectively, in the illustrated embodiment. In the illustrated embodiment, both of the inner ring 110 and the outer ring 130 are generally circular. In other embodiments, a top or plan view of at least one of the outer ring 110 and the inner ring 130 is not circular, for example, oval, elliptical, D-shaped, and the like. Furthermore, in the illustrated embodiment, the outer ring 110 and the inner ring 130 generally have the same diameter. In other embodiments, the outer ring 110 and the inner ring 130 independently have different diameters, sizes, and/or shapes. For example, some embodiments of the inner ring 110 have a smaller diameter than the outer ring 130, while in other embodiments, the inner ring 110 has a larger diameter than the outer ring 130. The flexible sheath 150 adopts the shape of the outer ring 110 and the inner ring 130. Consequently, the flexible sheath 150 in the illustrated embodiment is generally cylindrical.

In the illustrated embodiment, the outer ring 110 comprises an annular axis around which the outer ring 110 is rotatable or invertible in a process through which the outer ring 110 is rolled through itself, as will be discussed in greater detail below. Consequently, the outer ring 110 comprises a flexible material. In some embodiments, the flexible material comprises one or more polymers, for example, flexible engineering plastics. In some embodiments, the flexible material comprises an elastomer, for example, a thermoplastic elastomer. In some embodiments, the outer ring 110 comprises a composite, for example, a polymer and a reinforcing material. Examples of suitable reinforcing materials include fibers, fabrics, and the like, which comprise at least one of polymer, metal, glass, ceramic, and the like. Embodiments of the outer ring 110 are molded and/or extruded as a single piece or as a plurality of pieces that are assembled into the outer ring 110.

Figure 1B:
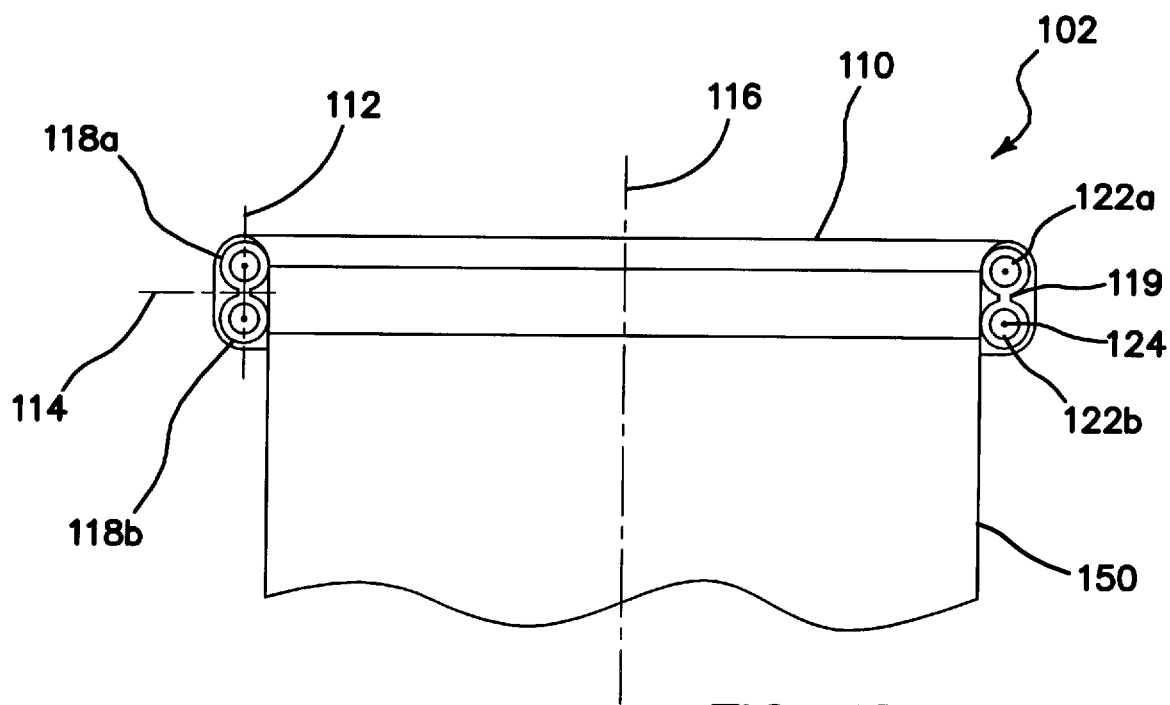
FIG. 1B is a side cross section of a proximal end of the retractor illustrated in FIG. 1A.
Figure 2A:
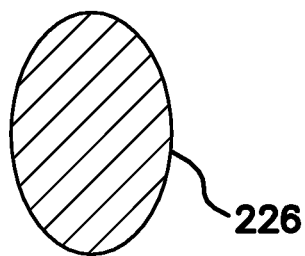
FIGS. 2A-2H and 2J-2K are cross sections of embodiments of outer rings.
Figure 2B:
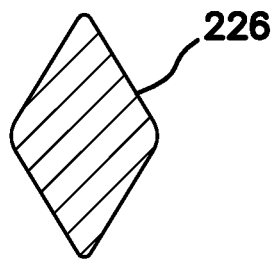
Figure 2C:
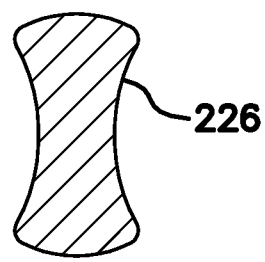
Figure 2D:
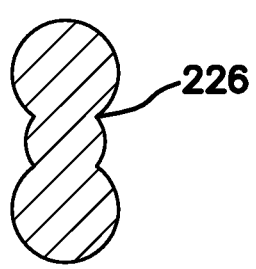
Figure 2E:
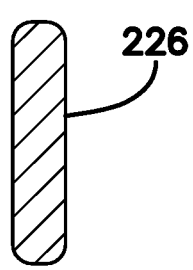
Figure 2F:
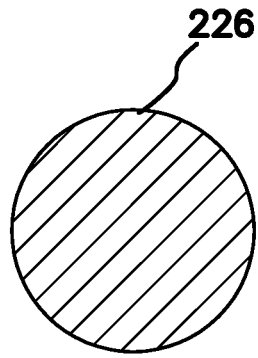
Figure 2G:
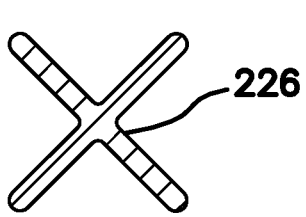
Figure 2H:
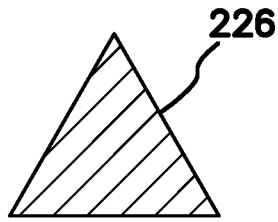
Figure 2J:
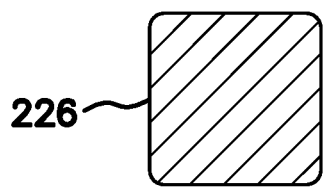
Figure 2K:
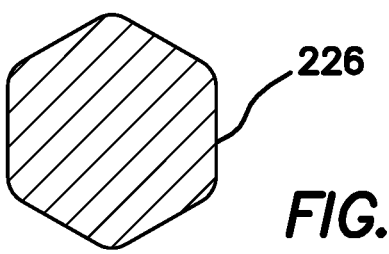

FIG. 1B illustrates a side cross section of the proximal end of the retractor 100. In the illustrated embodiment, a cross section of the outer ring 110 comprises a major or longer axis 112 and a minor or shorter axis 114. The major axis 102 is generally parallel with a longitudinal axis 118 of the outer ring 110, while the minor axis is generally parallel with a radial axis thereof. In other embodiments, the relative positions of the major 112 and minor 114 axes are reversed. As best viewed in FIG. 1B, which is a side cross-section of the outer ring 110, the outer ring 110 comprises a plurality of lumens: a first lumen 122a disposed on the major axis above the minor axis, and a second lumen 122b, disposed on the major axis below the minor axis. Consequently, the first lumen 122a is disposed above the second lumen 122b in the illustrated embodiment. Some embodiments of the outer ring 110 comprise a different number of lumens, for example, one lumen, three lumens, or even more lumens.

In the illustrated embodiment, a cross-sectional shape of the outer ring 110 is generally a figure-8, or first circle 118a and a second circle 118b joined by a web 119 extending therebetween. The first lumen 122a is disposed in the first circle 118a, and the second lumen 122b is disposed in the second circle 188b. Other embodiments of the outer ring have different cross-sectional shapes, for example as illustrated in FIGS. 2A-2K, generally oval or elliptical (FIG. 2A); diamond-shaped or rhomboid (FIG. 2B); hourglass or dog bone shaped (FIG. 2C); snowman-shaped (FIG. 2D); radially flat (washer-shaped outer ring), longitudinally flat (cylindrical outer ring), or flat at another angle (frustoconical outer ring) (FIG. 2E); circular (toroidal outer ring) (FIG. 2F), X-shaped (FIG. 2G), triangular (FIG. 2H), square (FIG. 2J), hexagonal (FIG. 2K), polygonal, and the like. Some embodiments of the outer ring comprise one or more gripping surfaces 226 that facilitate manually rolling the outer ring around the annular axis thereof. Examples of suitable gripping surfaces include generally flattened surfaces as shown in embodiments FIGS. 2A, 2B, 2E, 2H, 2J, and 2K; and concave surfaces as shown in embodiments FIGS. 2C, 2D, and 2G. Any of the embodiments illustrated in FIGS. 2A-2K optionally comprise one or more circumferential lumens in which wires or hoops are optionally disposed, as discussed below. Some embodiments of the outer ring 110 have a Möbius configuration in which the outer ring 110 is fabricated with a preloaded circumferential torsional stress, for example, by twisting an elongate member followed by joining the ends.

In some embodiments, a wire or rod 124 is disposed in at least one of the first lumen 122a and the second lumen 122b as illustrated in FIG. 1B. Embodiments of the wire or rod 124 in which the ends thereof contact or nearly contact each other in the lumen are referred to herein as a "split hoop". Some embodiments comprise a split hoop in each of the first lumen 112 and the second lumen 114. In some embodiments comprising a single split hoop 124, the split hoop 124 defines the annular axis. In some embodiments comprising a plurality of split hoops 124, rotating the outer ring 110 around the annular axis sequentially subjects each split hoop 124 to compression followed by then tension. In these embodiments, the split hoop 124 under compression defines the annular axis for that portion of the rotation.

In some embodiments, the split hoop(s) 124 are substantially non-compliant under the conditions under which the retractor 100 is used. In some of these embodiments, the split hoop(s) 124 render the outer ring 110 substantially non-compliant, for example, resisting compression. In other embodiments, the split hoop(s) 124 are compliant and the outer ring 110 is also compliant. Some embodiments of the outer ring 110 do not comprise a rod or wire disposed in a lumen thereof. Some embodiments of a non-compliant outer ring 110 facilitate direct coupling of another device to the outer ring 110 for example, a lid, cap, and/or gel cap. Some embodiments of a compliant outer ring 110 conform to a body surface.

Some embodiments of the outer ring 110 comprise a solid or non-split hoop 124 disposed in a lumen. As discussed above, in some embodiments, the solid hoop 124 defines an annular axis around which the outer ring 110 is rotatable. Some embodiments of the outer ring 110 comprise a solid hoop and at least one split hoop. In some embodiments, the solid hoop and/or split hoop maintains the top- or plan-view shape of the outer ring 110, for example, circular, oval, elliptical, or D-shaped, and/or maintain a side-view profile, for example, flat, curved, or saddle-shaped. In some embodiments, the hoop(s) 124 influence the rotational characteristics of the outer ring 110, for example, preventing rotation or permitting rotation, as discussed below. In some embodiments, the hoop(s) 124 influence the orientation of the outer ring 110, for example, with the major axis 112 parallel with the longitudinal axis 116 of the outer ring 110, as illustrated in FIG. 1B, or with the major axis 112 perpendicular with the longitudinal axis 116.

In some embodiments, a profile or graph of a potential energy of the outer ring 110 versus rotation around the annular axis over 360° comprises at least one lower energy rotational position and at least one higher energy rotational position. For example, the configuration illustrated in FIGS. 1A and 1B is the lower energy rotational position for the illustrated embodiment. In the illustrated embodiment, in each 360° rotational cycle, the outer ring 110 has two lower energy rotational positions, or potential energy valleys, about 180° apart in which the major axis is generally parallel with the longitudinal axis thereof, and two higher energy rotational positions or potential energy peaks about 180° apart in which the major axis is generally parallel with the radial axis thereof. Consequently, the higher energy and lower energy rotational positions are about 90° apart. Some embodiments of the outer ring 110 have a potential energy profile that is generally sinusoidal, while the potential energy profile of other embodiments of the outer ring 110 has a different shape, for example, generally saw-tooth, step-function, combinations thereof, or another suitable profile. Embodiments of outer rings 110 with different cross-sectional shapes have different potential energy profiles.

A consequence of the potential energy profile discussed above is referred to as "snap action" in the annular rotation of the outer ring 110. Absent any applied rotational force, the outer ring 110 adopts a low energy geometry or potential energy valley as an equilibrium or detent position. Applying an annular torque to the outer ring 110 rotates or rolls the outer ring 110 around the annular axis, thereby increasing the potential energy of the outer ring 110, until the outer ring 110 reaches the higher energy rotational position and potential energy peak. As the outer ring 110 passes over the potential energy peak, the stored potential energy therein is released as the outer ring 110 "snaps-to" or adopts the lower energy rotational position in falling into the next potential energy valley. Consequently, the outer ring 110 resists rotation out of the low energy rotational positions and snaps into the low energy rotational or detent positions when perturbed therefrom.

In a first direction of rotation referred to as "inversion" or "rolling in", the top of the outer ring 110 passes downwardly through the opening thereof. In a second direction of rotation referred to as "eversion" or "rolling out", the bottom of the outer ring 110 passes upwardly through the opening thereof. In some embodiments, the potential energy profile is generally symmetrical with respect to the direction of rotation. In other embodiments, the potential energy is not symmetrical, for example, steeper from valley to peak when rotating in one direction than when rotating in the opposite direction. For example, in some embodiments, inversion requires a greater force than eversion. Some embodiments of outer rings 110 with unsymmetrical potential energy profiles have unsymmetrical cross sections.

Figure 3:
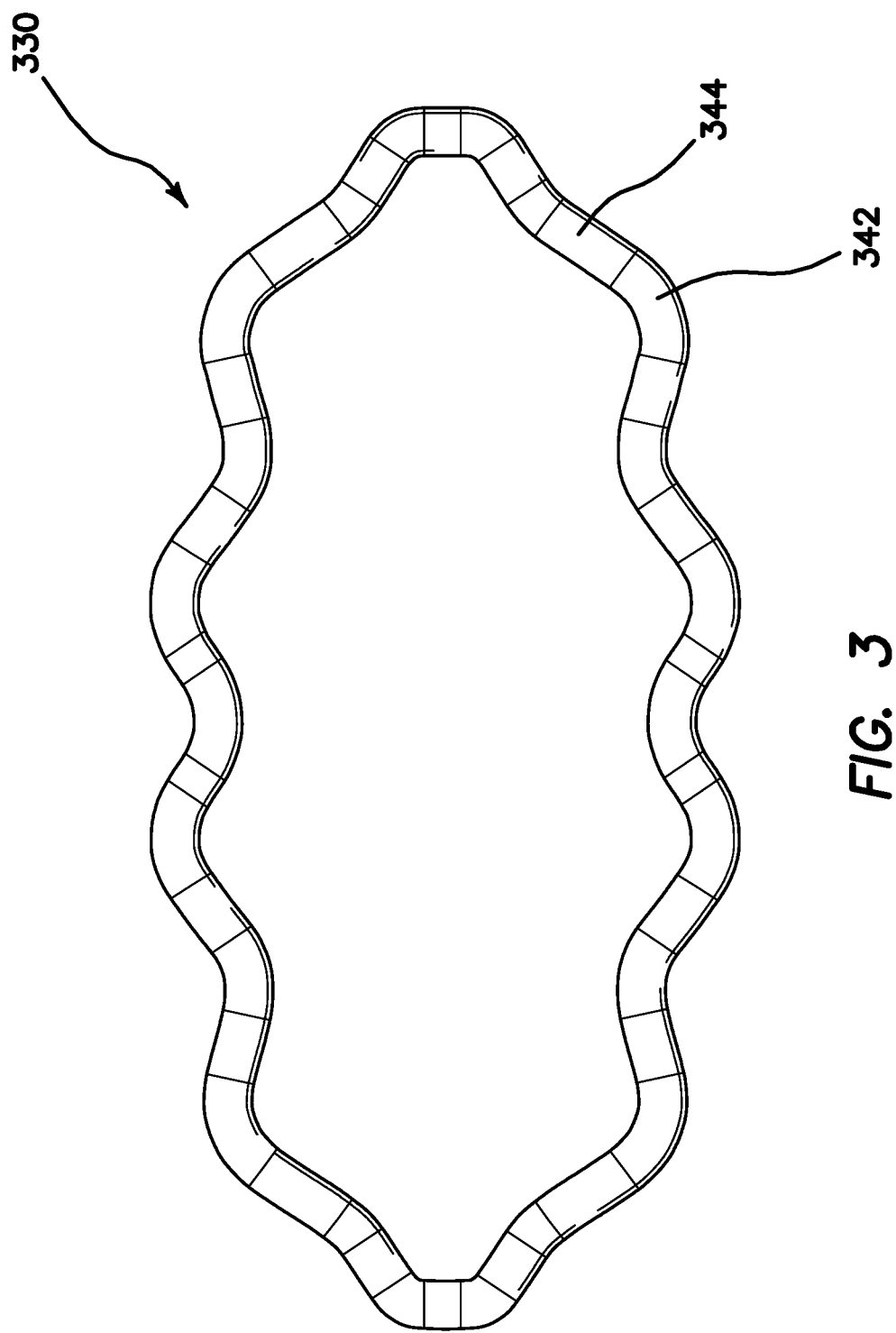
FIG. 3 is a perspective view of an embodiment of a reshapeable inner ring.

Returning to FIG. 1A, the inner ring 130 is deformable, comprising a flexible material, for example, a polymer for example, a flexible engineering plastic. In some embodiments, the polymer is an elastomer, for example, a thermoplastic elastomer. In some embodiments, the inner ring 130 is reshapeable, for example, comprising a plastically deformable or malleable elements, for example, metal and/or shape memory wires, strips, mesh, and the like. In some embodiments, the deformable elements are pleated or folded, for example, in an accordion fold or a fan fold. Some embodiments of the reshapeable inner ring 130 comprise clay, powders, granules, beads, and the like disposed in a covering or envelope. Some embodiments of the reshapeable inner ring 130 comprise linked elements—for example, a link chain, a ball-and-socket chain, or a roller chain—covered, for example, with a flexible polymer. FIG. 3 is a perspective view of an embodiment of a reshapeable inner ring 330 comprising linked, alternating arcuate members 342 and straight members 344, disposed end-to-end, defining a closed loop. Each arcuate member 342 is rotatable relative to an adjacent straight member 344 around a local longitudinal axis, resulting in a reshapeable inner ring 330. Other embodiments comprise different numbers of arcuate 342 and straight 344 members. In some embodiments, the length of each of the arcuate 342 and straight 344 members is independently selected. In some embodiments the angle subtended by each arcuate member 342 is independently selected. Some embodiments comprise fewer or no straight members 344. In some embodiments, a conformation of the inner ring 330 is lockable, for example, by applying tension or compression to the inner ring 330. Reshapability permits a user to conform the inner ring 330 to the anatomy of the patient when placing the inner ring 330.

Figure 4A:
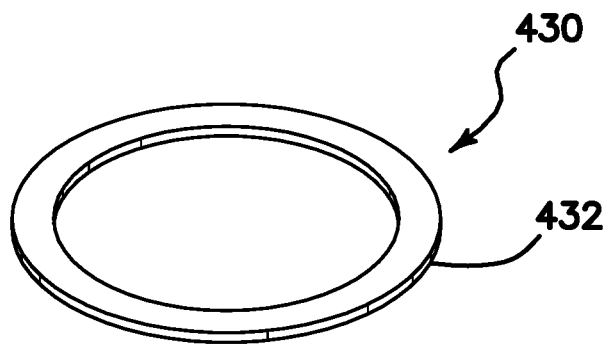
FIGS. 4A and 4B are perspective views of embodiments of inner rings with thinned edges.
Figure 4B:
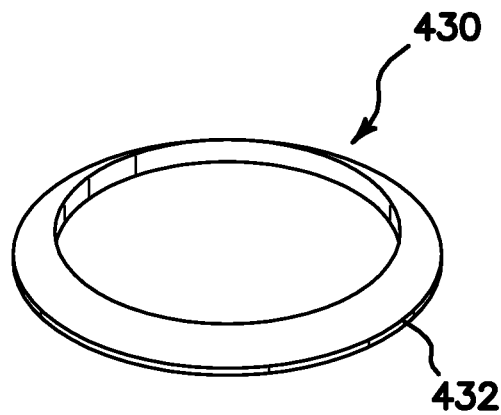

In the embodiment illustrated in FIG. 1A, a cross section of the inner ring 130 is generally circular. In other embodiments, the inner ring 130 has another cross section, for example, oval, elliptical, flat, D-shaped, or any profile illustrated in FIGS. 2A-2K for the outer ring 110. The cross section of some embodiments of the inner ring is thinned and/or flattened at least at the outer edge 432, for example, a flat or thin wedge, resulting in an inner ring 430 with a washer-like shape as shown in FIGS. 4A and 4B. The flattened outer edge permits a user to manipulate the edge into tight spaces when placing the inner ring 430, for example, between muscle layers. Embodiments of the inner ring 130 are molded and/or extruded as a single piece, or as a plurality of pieces that are assembled into the inner ring 130.

Some embodiments of the inner ring 130 are collapsible and/or foldable, which facilitates inserting and/or removing the inner ring 130 through an incision or opening. For example, some embodiments comprise at least one notch, hinge, and/or weak point, which facilitates folding thereof. Some embodiments of the inner ring 130 disassemble, thereby permitting collapse of the inner ring 130. For example, in some embodiments, the inner ring 130 comprises a member comprising two free ends that are brought together and coupled, thereby circularizing the inner ring 130. In some of these embodiments, the coupled free ends are disassembled, thereby collapsing the inner ring 130. In some embodiments, the free ends are coupled using a mechanical fastener, for example, at least one of a pin, a clip, a clasp, key, or the like. In some embodiments, the fastener comprises a breakable element, for example, a tab, that bridges the free ends. Disengaging or breaking the fastener uncouples the free ends.

Figure 5:
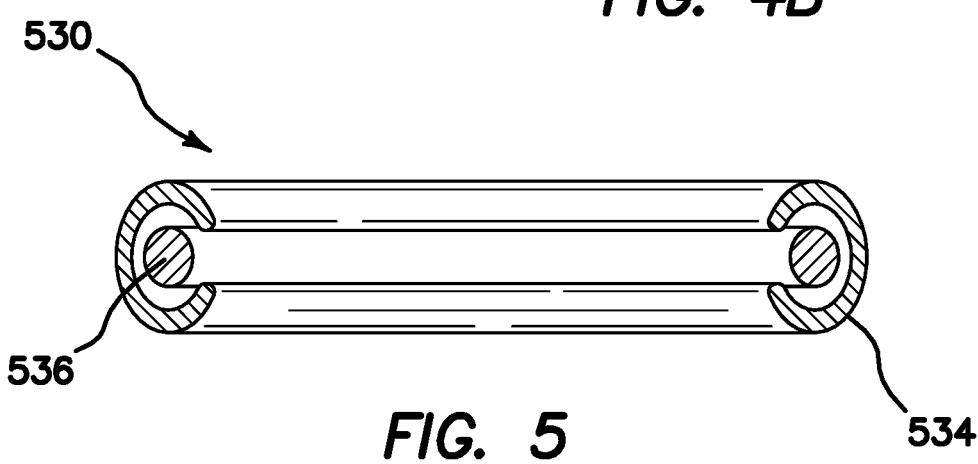
FIG. 5 is a partial cross section of an embodiment of a collapsible inner ring.

In other embodiments, the inner ring 130 comprises an annular member coupled to a stiffening member. Disengaging and/or removing the stiffening member permits the annular member to collapse. For example, in some embodiments, the stiffening member comprises a ring-shaped portion around which the annular member is engaged. For example, in the embodiment illustrated in FIG. 5, the annular member 534 of the inner ring 530 comprises a C-shaped cross section with the opening of the C-shape generally facing the longitudinal axis of the annular member 534, and at least a portion of the stiffening member 536 fits within the C-shape. In other embodiments, the opening of the C-shape faces another direction, for example, proximally, distally, or away from the longitudinal axis. Removing the stiffening member 536, for example, by pulling on a tether secured thereto, as discussed below, permits collapsing the annular member 534. In other embodiments, the stiffening member engages only a portion of the annular member. Again, removing the stiffening member permits collapsing the annular member.

In some embodiments, the inner ring 130 is inserted into a body cavity in the collapsed or folded state, then reconfigured into the retracting or deployed state therein.

Some embodiments of the inner ring 130 comprise a tether secured thereto. The tether facilitates removal of the inner ring 130, for example, by pulling. In some embodiments, the tether facilitates folding or collapsing the inner ring. For example, in some embodiments, pulling the tether draws together portions of the inner ring 130 on either side of a notch, hinge, or weak point thereof, thereby folding the inner ring 130 and facilitating removal thereof. In some embodiments, the tether is secured to a mechanical fastener coupling the free ends of the inner ring 130 together. For example, in some embodiments, the tether removes or pulls free a pin, clip, or clasp, thereby unsecuring the free ends from each other. In some embodiments, the tether is coupled to a break-away element bridging the free ends of the inner ring 130 and breaks the break-away element when pulled, thereby unsecuring the free ends. In some embodiments, the tether is secured to a stiffening member of the inner ring 130, and pulling the tether disengages the stiffening member from the annular member, thereby permitting the annular member to collapse.

In the embodiment illustrated in FIGS. 1A and 1B, the sheath 150 is generally a cylindrical tube with a diameter substantially equal to inside diameters of the outer ring 110 and the inner ring 130. In other embodiments, the sheath 150 is not cylindrical, for example, frustoconical, hourglass-shaped, D-shaped, oval, combinations, and the like. In some embodiments, the sheath 150 is fabricated as a seamless tube. In other embodiments, the sheath 150 comprises at least one seam. In some embodiments, the sheath 150 comprises longitudinal pleats. In some embodiments, the sheath 150 comprises at least one longitudinal slit. In some embodiments, the sheath 150 comprises a plurality of bands, strips, and/or sheets extending between the outer ring 110 and the inner ring 130. The bands, strips, and/or sheets extend longitudinally and/or at a bias. In some embodiments, edges of adjacent bands, strips, and/or sheets overlap, thereby defining a tubular structure. In some embodiments, the sheath 150 comprises both a tubular component as well as at least one band, strip, and/or sheet. In some of these embodiments, at least some of the edges of adjacent bands, strips, and/or sheets do not overlap. A first end of the sheath 150 is coupled to the outer ring 110 and a second end of the sheath 150 is coupled to the inner ring 110.

The flexible sheath 150 comprises an abrasion and/or puncture resistant material. The abrasion and/or puncture resistance of the sheath 150 improves the performance and reliability of the retractor 100 in procedures using sharp and/or pointed instruments, and/or prosthetic device, for example, in orthopedic procedures including hip procedures, hip replacement, and spinal procedures. Some of these procedure use instruments such as chisels, drills, rasps, scalpels, and the like. Embodiments of the retractor 100 are also useful in other types of procedures, for example, arthroscopic surgery, and even abdominal surgery. Embodiments of the abrasion and/or puncture resistant the sheath 150 protect the incision and/or opening in the body wall and surrounding tissue from damage from the instruments used in the surgical procedure. Some embodiments of the sheath 150 also reduce contamination in the surgical site, for example, from external bacteria, from tissues removed from the patient's body, and from surgical instruments and supplies.

Embodiments of at least one portion of the sheath material have a puncture resistance of at least about 16 N (3.6 lb) under FED-STD-101/2065 (Puncture Resistance and Elongation Test). Some embodiments of the sheath material have a puncture resistance of at least about 20 N (4.5 lb), at least about 30 N (6.7 lb), at least about 40 N (9 lb), at least about 50 N (11 lb), at least about 60 N (13.5 lb), or at least about 100 N (22.5 lb).

Example 1

Puncture resistance was measured according to FED-STD-101/2065 for a polyurethane laminated fabric (PUL-2 mil, Seabright) comprising a polyester knit fabric and a 50 μm (2 mil) polyurethane layer laminated to one face of the fabric. In the test, a 3.175 mm (0.125 in) rounded shaft was contacted with a 7.6 cm×7.6 cm (3 in×3 in) fabric sample at 7.6 cm/min (3 in/min). The force at penetration is the penetration resistance. The test was performed on 15 samples with the rounded shaft contacting the polyester face of the fabric with an average puncture resistance of 61.07 N (13.73 lb). The average puncture resistance for 15 tests on the polyurethane side was 53.56 N (12.04 lb).

Example 2

Puncture resistance of a 76 μm (4 mil) polyether polyurethane film (PELLETHANE® 2363, Lubrizol) used in current retractor sheaths was measured as above. The average for 15 tests was 12.46 N (2.80 lb).

Embodiments of the sheath comprise sheets, membranes, fibers, and/or strands of one or more materials that endow the sheath with the abrasion and puncture resistance. Suitable sheets, membranes, fibers, and/or strands comprise at least one of natural polymers, semi-synthetic polymers, synthetic polymers, metal, ceramic, glass, carbon fiber, carbon nanotubes, and the like. Suitable natural polymers include cellulose, silk, and the like. Semi-synthetic fibers include nitrocellulose, cellulose acetate, rayon, and the like. Suitable synthetic fibers include polyester, aromatic polyester, polyamide (NYLON®, DACRON®), aramid (KEVLAR®), polyimide, polyolefin, polyethylene (SPECTRA®), polyurethane, polyurea, polyvinyl chloride (PVC), polyvinylidene chloride, polyether amide (PEBAX®), polyether urethane (PELLETHANE®), polyacrylate, polyacrylonitrile, acrylic, polyphenylene sulfide (PPS), polylactic acid (PLA), poly(diimidazopyridinylene-dihydroxyphenylene) (M-5); poly(p-phenylene-2,6-benzobisoxazole) (ZYLON®), liquid crystal polymer fiber (VECTRAN®), and the like, and blends, copolymers, composites, and mixtures thereof. Suitable metals include stainless steel, spring steel, nitinol, super elastic materials, amorphous metal alloys, and the like.

Figure 6:
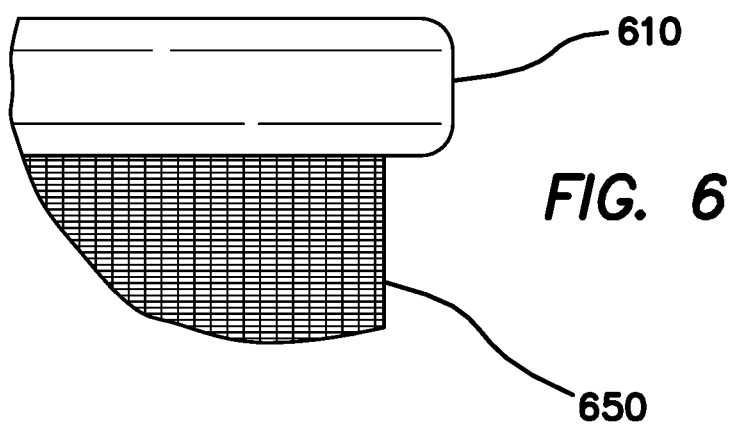
FIG. 6 is a detailed view of a proximal end of a retractor comprising a woven fabric sheath.

FIG. 6 is a detailed view of a portion of the outer ring 610 and sheath 650, which comprises a fabric or textile. In some embodiments, the fabric or textile comprises, for example, at least one of a woven fabric, a non-woven fabric, a knit fabric, a double-knit fabric, a mesh, a braided fabric, and a braided mesh fabric. Suitable fabrics comprise monofilament fibers and/or yarns. Other suitable fabrics comprise twisted and/or braided yarns. Suitable yarn materials are described in the previous paragraph. Some embodiments of the fabric comprise a combination of fibers, for example, different warp and weft yarns in woven or mesh fabrics, or a combination of yarns in knit or braided fabrics. Some embodiments of the fabric are substantially nondistensible, while other embodiments are distensible. In some embodiments, the fabric resists tear propagation in the event of damage thereto, for example, from inadvertent puncturing or cutting by a surgical instrument, or from purposeful puncturing in securing the sheath 150 as described below. Examples of such fabrics include rip-stop fabrics, certain knits, double knits, and braided mesh fabrics. In some embodiments, the orientation of fabric reduces the likelihood of snagging or otherwise obstructing an instrument as it is inserted through the sheath. For example, in some embodiments, a smoother surface of the fabric faces a longitudinal axis or inside of the sheath. In some embodiments, the fabric is oriented on a bias, or with ridges or troughs generally parallel with the longitudinal axis of the sheath. Examples of suitable fabrics include rip-stop polyamide (Nylon®), Oxford weave fabrics, abrasion-resistant polyester and/or polyamide fabrics (Cordura®), braided monofilament fabrics, and the like.

Some embodiments of the sheath material comprises a composite comprising a fabric or textile, for example, at least one of a coated fabric, a laminated fabric, and a fabric embedded in a polymer. Coatings and/or laminations are disposed on one face or both faces of the fabric. Suitable coatings and laminating materials include polymers, for example, at least one of polyurethane, polyether, PVC, polyvinylidene chloride, silicone, styrene-butadiene, polyethylene, polypropylene, ethylene-propylene copolymer, polyisoprene, ethylene vinyl acetate (EVA), ethylene-propylene-diene monomer (EPDM), polyamide (MYLAR®), polyether block amide (PEBAX®), polyether urethane (PELLETHANE®), composites, blends, mixtures, and the like. An example of a suitable composite fabric is polyurethane laminated fabric (PUL). Some embodiments of the coating or lamination modify gas and/or moisture permeability through the sheath material, for example, by controlling the size of pores therethrough. For example, decreasing moisture permeability reduces dehydration of the retracted tissue and/or creates a barrier to pathogens such as bacteria. Increasing gas and moisture permeability permits hydrating and/or oxygenating the retracted tissue. Some materials are selectively permeable to certain fluids. For example, some embodiments of PVC are oxygen permeable and moisture impermeable, thereby permitting simultaneously oxygenating tissue while reducing dehydration. Some embodiments of the coating or lamination comprise an antibacterial or antimicrobial agent. In some embodiments, the antibacterial or antimicrobial agent is a surface agent or is integral to the material. Examples of suitable antibacterial or antimicrobial agents include iodine, antibiotics, silver, triclosan, biocides, and the like. Some embodiments of the coating or lamination provide a smoother and/or lower friction inside surface, which reduces the likelihood of instrument damage to the sheath 150.

Some embodiments of the sheath 150 comprise a composite comprising a fiber-reinforced polymer film or membrane. Suitable fibers or strands are discussed above. Suitable polymer film materials include at least one of materials discussed above as coating and laminating materials. In some embodiments, the fibers are sandwiched between polymer film layers. In some embodiments, the polymer film layers are independently selected. For example, in some embodiments, the outer layer provides desirable tissue contact properties discussed above, while the inner layer is puncture resistant.

Some embodiments of the sheath 150 comprise a plurality of layers, for example, a fabric layer and a polymer film layer, or a fabric layer sandwiched between polymer film layers. In some embodiments, the layers are secured to each other. In other embodiments, the layers are independent of, or not secured to each other, for example, a polymer film layer and a layer comprising a plurality of strips or bands as discussed above.

Some embodiments of the sheath 150 comprise a fluid-permeable layer disposed on a fluid-impermeable layer, with the fluid-impermeable layer disposed on the inside of the sheath 150. The fluid-permeable layer contacts the wound margins, thereby permitting a user to supply pressurized fluid and/or apply vacuum to the wound margins. For example, in some embodiments, oxygen, moisture, therapeutic agent, and/or other fluids are supplied to the wound margins. In some embodiments, applying vacuum promotes bleeding, thereby reducing tissue necrosis. Embodiments of the fluid-permeable layer comprise at least one of open cell foam, fabrics, non-woven fabrics, and knit fabrics.

In other embodiments, the sheath 150 is stretchable longitudinally. In some embodiments, longitudinal and circumferential stretch characteristics of the sheath 150 are the same, that is, the stretch is isotropic. In other embodiments, longitudinal and circumferential stretch characteristics of the sheath 150 are different, that is, the stretch is anisotropic. For example, in some embodiments, the sheath 150 has greater circumferential stretch than longitudinal stretch.

In other embodiments, the sheath 150 has substantially no or little longitudinal stretch, that is, is non-distensible longitudinally. Consequently, a retraction force exerted on an incision or opening by the sheath 150 remains substantially constant over the course of a procedure. In some embodiments, the sheath 150 is radially or circumferentially expandable. For example, some embodiments of a tubular sheath 150 comprise a woven material, as discussed below, that is expandable or stretchable circumferentially, that is, perpendicular to the longitudinal axis. Some embodiments comprise an elastomeric membrane or film, and longitudinal non-stretchable elements. For example, some embodiments of the sheath 150 comprise a composite comprising an elastomeric film and longitudinally disposed, non-stretchable fibers, as discussed above. The fibers make the sheath 150 longitudinally non-stretchable, while the polymer film permits radial expansion. Embodiments of the sheath 150 comprising non-stretchable longitudinal strips and an elastomeric membrane are also longitudinally non-stretchable and radially expandable. Embodiments of a sheath 150 comprising a non-stretchable tube comprising one or more longitudinal slits and/or pleats are longitudinally non-stretchable and radially expandable. Embodiments of a sheath 150 comprising a plurality of non-stretchable longitudinal strips or bands are also longitudinally non-stretchable and radially expandable.

In some embodiments, at least a portion of the sheath 150 is transparent or transparent, thereby providing a view of the retracted tissue. In some embodiments comprising a polymer membrane or film, the polymer membrane or film is transparent or transparent.

In some embodiments, the sheath 150 comprises a proximal portion 152 with different properties than a distal portion 154 thereof. For example, in some embodiments, the proximal portion 152 has greater flexibility than the distal portion 154, thereby facilitating winding or rolling the sheath 150 around the outer ring 110. In other embodiments, the proximal portion 152 comprises one of a hook and a loop of a hook-and-loop fastener, thereby providing adjustability in embodiments using hook-and-loop fasteners, discussed below. Some embodiments of the sheath 150 further comprise a middle portion 156 disposed between the proximal 152 and distal 154 portions. For example, some embodiments of the proximal portion 152 and the distal portion 154 of the sheath comprise a tear-resistant material for use with outer rings 110 and inner rings 130 comprising teeth, as described below. In some embodiments, the proximal portion 152 and the distal portion 154 of the sheath comprise an elastomeric material, and the middle portion comprises a longitudinally non-distensible material, as described above.

Figure 7A:
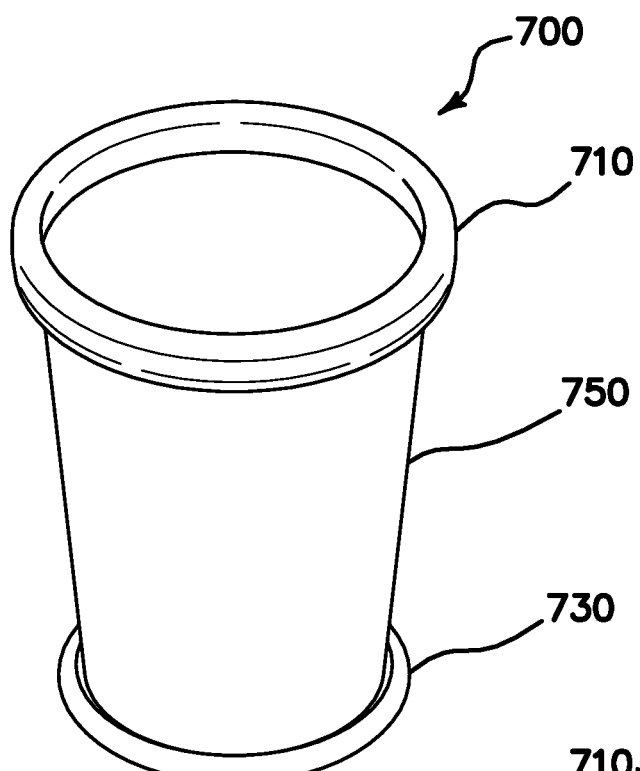
FIG. 7A is a perspective view of another embodiment of a retractor.
Figure 7B:
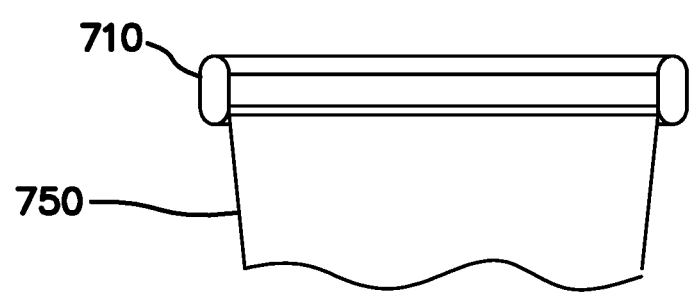
FIG. 7B is a side cross section of a proximal end of the retractor illustrated in FIG. 7A.
Figure 7C:
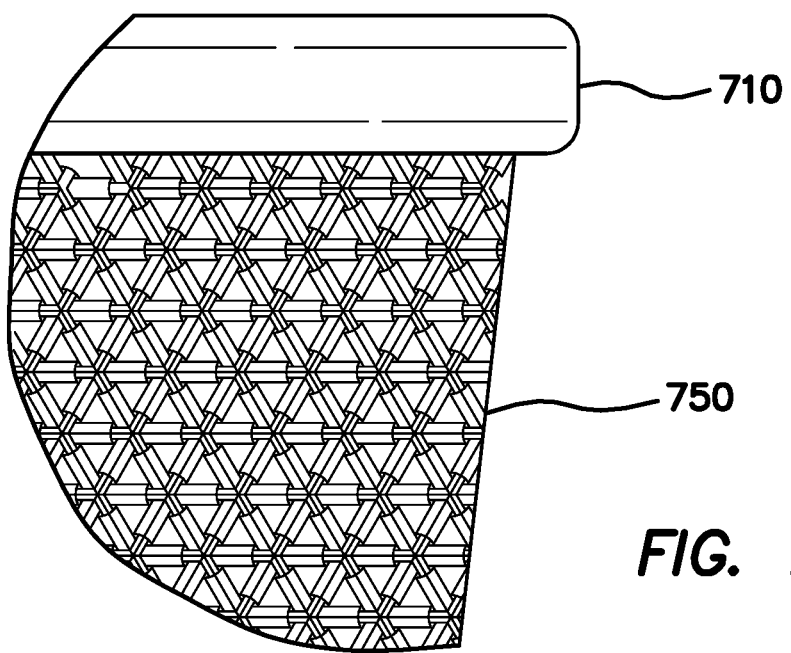
FIG. 7C is a detail view of an outer ring and sheath of the retractor illustrated in FIG. 2A.

FIG. 7A is a perspective view and FIG. 7B is a side cross section of another embodiment of a wound retractor 700 that is generally similar to the embodiment described above. The retractor 700 comprises an outer ring 710, an inner ring 730, and a sheath 750. In the illustrated embodiment, the outer ring 710 has a larger diameter than the inner ring 730. Consequently, the sheath 750 is generally frustoconical or funnel-shaped, tapering or converging from a proximal end, coupled to the outer ring 710, to a distal end, coupled to the inner ring 730. Also, the outer ring 710 has a generally oval shape rather than the figure-8 shape of the embodiment illustrated in FIGS. 1A and 1B. As shown in a detailed view of the outer ring 710 and sheath 750 in FIG. 7C, the sheath 750 comprises a knit fabric in the illustrated embodiment.

The embodiment of the retractor 700 is useful in procedures in which the inner ring 730 is inserted through a smaller body opening. The larger outer ring 710 improves protection of the body opening and surrounding tissue. Examples of such procedures include orthopedic hip replacement, vaginal retraction, and rectal retraction.

Other embodiments of the retractor comprise at least one of an outer anchor member and an inner anchor member different from the embodiments described above.

Figure 8A:
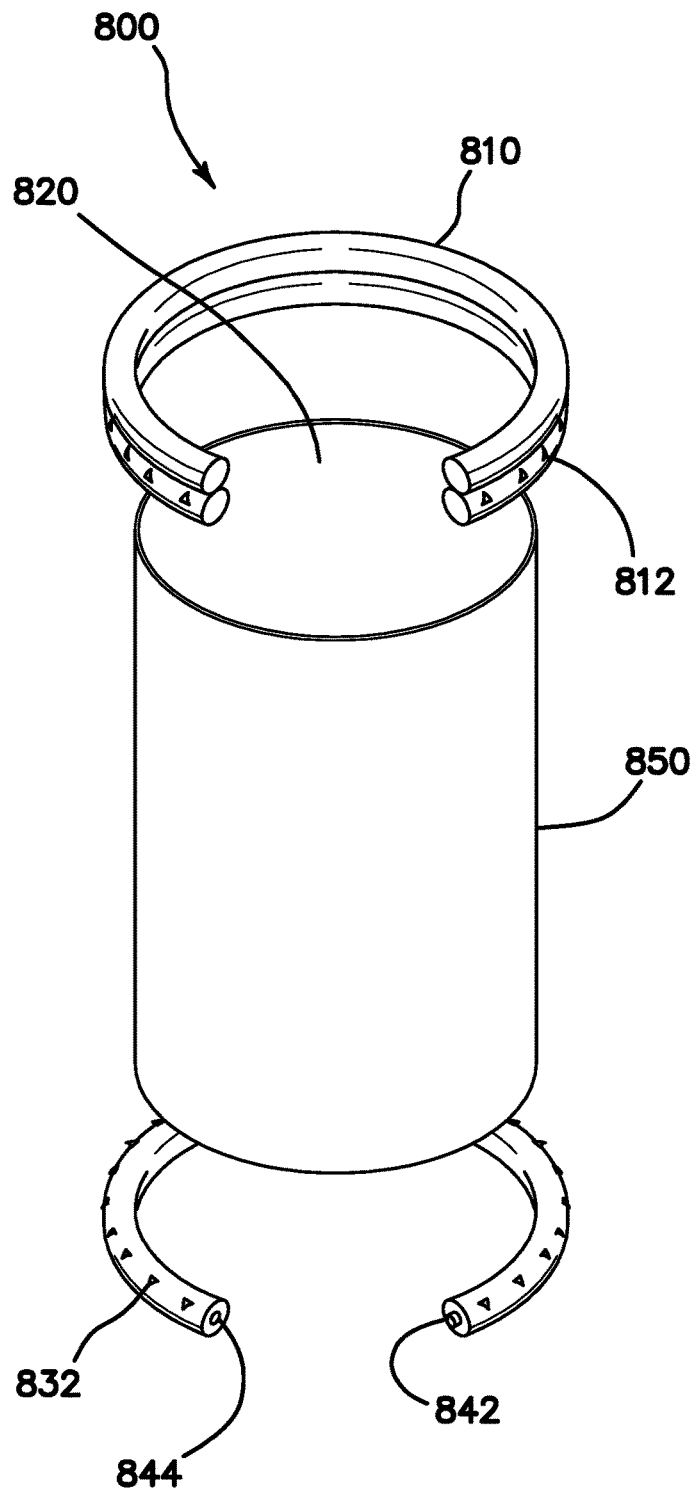
FIG. 8A is a perspective view of another embodiment of an unassembled retractor kit.

FIG. 8A illustrates a perspective view of another embodiment of a retractor 800 generally similar to the embodiments described above. In the illustrated embodiment, an outer ring 810, inner ring 830, and sheath 850 are unassembled. The illustrated retractor 800 is provided as separate components, which are assembled by the user. For example, in some embodiments, individual components are selected from a kit according to the requirements of a particular procedure. For example, embodiments of the kit comprise at least one of outer rings 810 with different diameters, inner rings 830 with different diameters, sheaths 850 with different diameters, sheaths 850 with different lengths, sheaths comprising different materials, and the like. In some embodiments, the retractor 800 is disassemblable, and one or more of the outer ring 810, the inner ring 830, and the sheath 850 is reusable, for example, autoclavable.

The outer ring 810 is illustrated in a non-circularized configuration. In the illustrated embodiment, ends of the non-circularized outer ring 810 are coupled using a coupler 820. The outer ring 810 comprises a plurality of fasteners 812, which secure the sheath 850 to the outer ring 810. The inner ring 830 is also in a non-circularized configuration, and comprises a circumferentially facing pin or peg 842 on a first end thereof, and a corresponding circumferentially facing opening 844 disposed on a second end. The inner ring 830 also comprises a plurality of fasteners 832, which secure the sheath 850 to the inner ring 830. In the illustrated embodiment, the fasteners 812 and 832 comprise hooks, which puncture the sheath 850, thereby securing the sheath to the outer ring 810 and inner ring 830, respectively. In some embodiments, the fasteners 812 and/or 833 are bendable, which permits a user to further secure the sheath 850. In other embodiments, each of the outer ring 810 and inner ring 830 independently comprises fasteners for the sheath 850, for example, hooks, clips, clamps, pins, wires, hook-and-loop fasteners, laces and eyelets, and the like. For example, in some embodiments, the fastener comprises a wire that passes through eyelets disposed on both the sheath 850, and the outer ring 810 or the inner ring 830. In other embodiments, the outer ring 810 and/or inner ring 830 comprises two interlocking rings that capture the sheath 850 therebetween, thereby securing the sheath thereto. In some embodiments, the interlocking rings snap together, screw together, clip together, and the like.

Figure 8B:
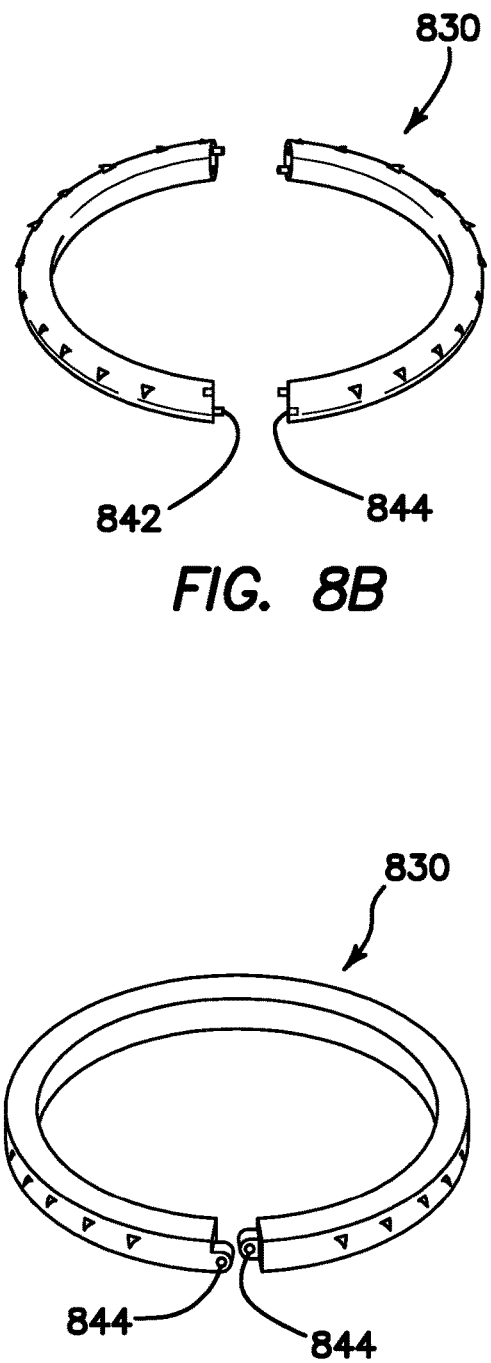
FIG. 8B is a detail view of another embodiment of an inner ring.

In the illustrated embodiment, the inner ring 830 comprises a pin-and-hole 842 and 844 system that couples together the free ends thereof. FIG. 8B is a perspective view of an inner ring 830 comprising another embodiment of a pin-and-hole system comprising a plurality of sections, each comprising pins 842 disposed on both ends of the inner ring 830 and corresponding, mating holes 844 disposed on both ends of the inner ring 830, which permit a user to couple the free ends of the inner ring 830.

Figure 8C:
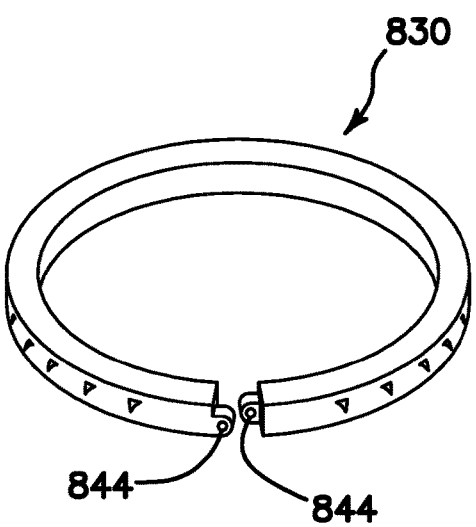
FIG. 8C is a perspective view of another embodiment of an inner ring.

FIG. 8C is a perspective view of another embodiment of an inner ring 830 comprising a pin-and-hole system comprising a radial hole 844 disposed on each free end of the outer ring 830, which together with a pin (not illustrated), couple the free ends of the inner ring 830. As discussed above, some embodiments of the retractor 800 comprise a tether suitable for pulling a pin free, thereby collapsing the inner ring 800.

Those skilled in the art will understand that similar arrangements for circularizing the outer ring 810 and the inner ring 830 described above conjunction with the embodiments illustrated in FIGS. 8A-8C are also applicable to the inner ring 830 and the outer ring 810, respectively. In the embodiment illustrated in FIG. 8A, the outer ring 810 is rotatable around an annular axis thereof. In other embodiments, the outer ring is not rotatable around an annular axis. In some of these embodiments, the sheath 850 is not tensioned by wrapping around the outer ring 810. Instead, the sheath 850 is threaded through a portion of the access channel extending through the center of the outer ring 850, then tensioned by pulling the sheath 850 distally from the inner ring 830. The tension is maintained by engaging the sheath 850 to the fasteners 812, hooks in the illustrated embodiment.

Figure 9A:
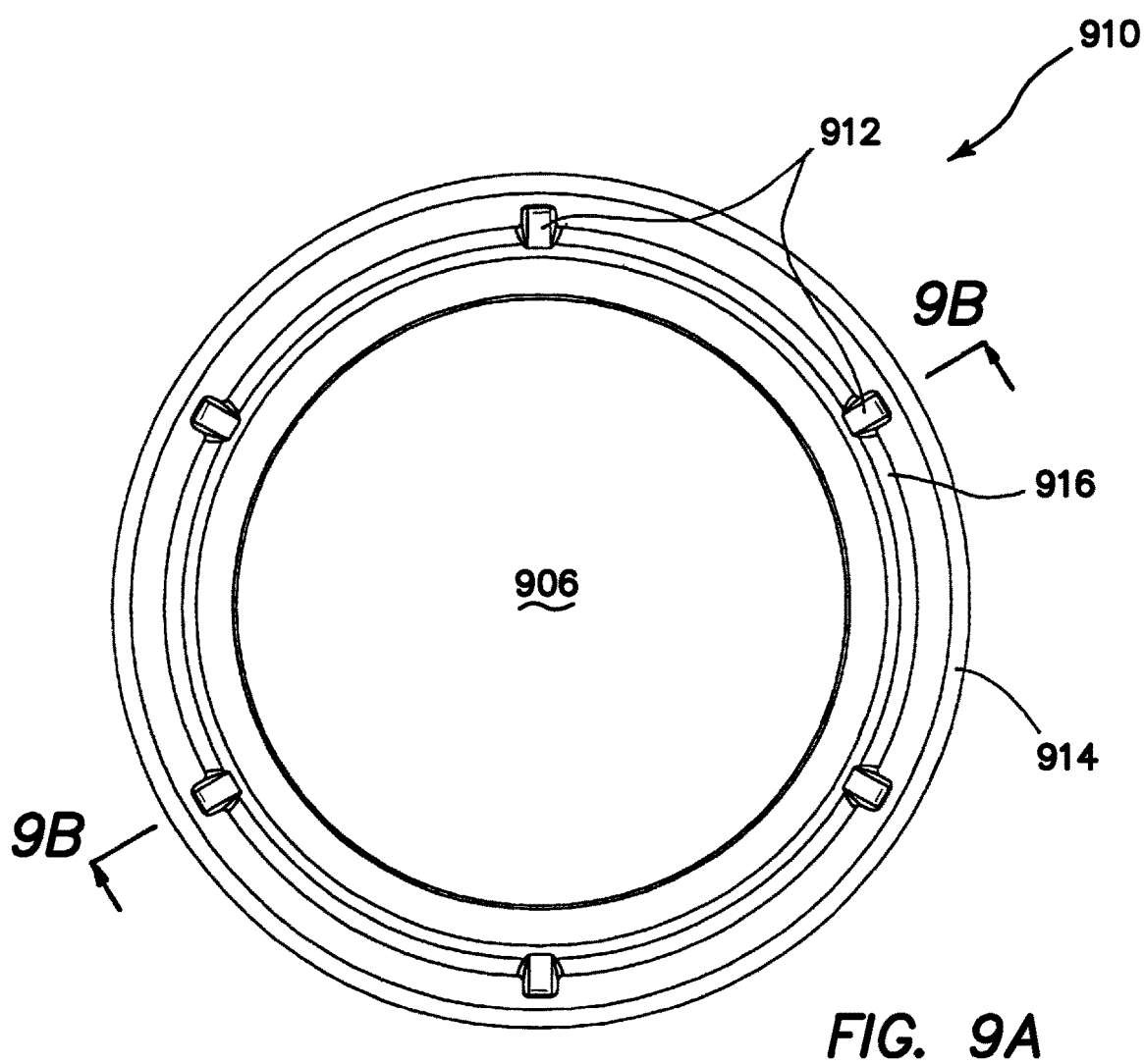
FIG. 9A is a top view and FIG. 9B is a side view of an embodiment of an outer ring.
Figure 9B:
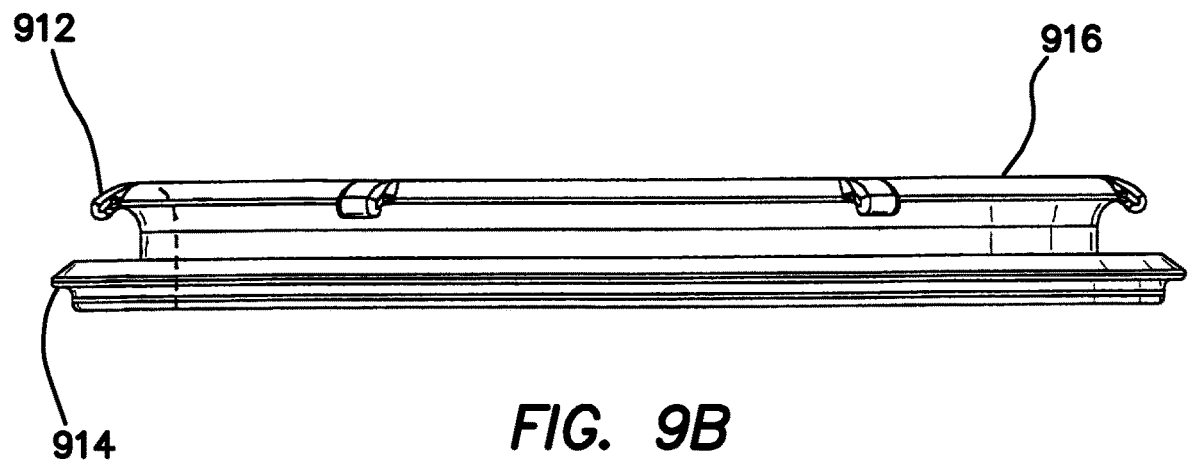

FIG. 9A is a top view and FIG. 9B is a side view of another embodiment of an outer ring 910 comprising a lower flange 914, a concentric upper flange 916, and a plurality of fasteners or hooks 912 extending radially outwards and distally from the upper flange 916. The outer ring 910 is rigid or semi-rigid and is not rotatable around an annular axis. In use, a proximal end of the sheath is threaded proximally out through a portion of an access channel 906 extending through the outer ring 910, pulled proximally, thereby tensioning the sheath, and the sheath engaged to the hooks 912, thereby maintaining a desired tension on the sheath. In the illustrated embodiment, the hooks 912 are blunt and do not penetrate the sheath. In other embodiments, the hooks 912 are pointed and penetrate the sheath.

Figure 10:
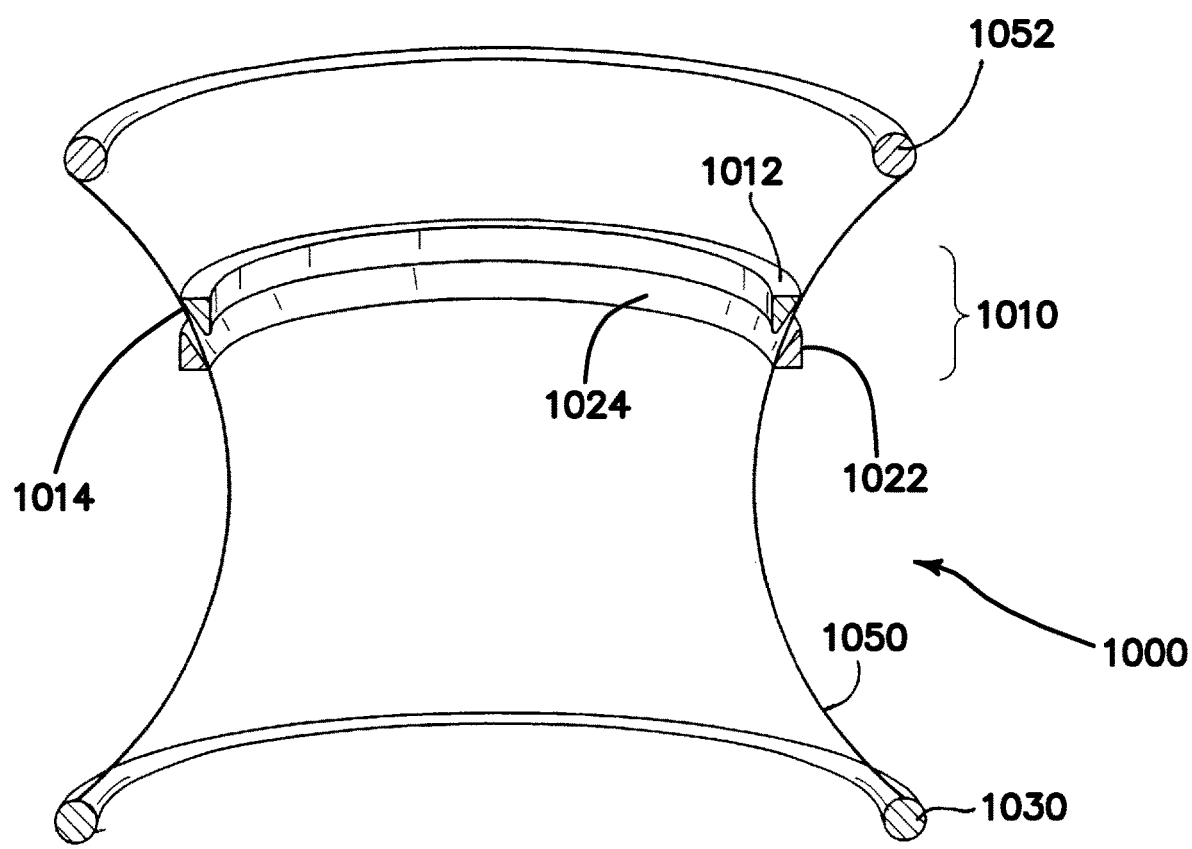
FIG. 10 is a partial side cross section of another embodiment of a retractor.

FIG. 10 is a side partial cross section of another embodiment of a retractor 1000, similar to the embodiments described above, comprising an outer anchor 1010, an inner anchor 1030 and a sheath 1050. In the illustrated embodiment, the outer anchor 1010 comprises a proximal ring 1012 and a distal ring 1022, which nest together. The nesting surfaces 1014 and 1024, respectively, are frustoconical or wedge-shaped, with a distal diameter smaller than a proximal diameter. In some embodiments, at least a portion of the nesting surfaces 1014 and 1024 comprise steps. With the sheath 1050 disposed between the proximal ring 1012 and the distal ring 1014 as shown in FIG. 10, pulling the sheath 1050 distally, for example, when the sheath 1050 is under tension while retracting tissue, draws the proximal ring 1012 distally, thereby seating the nesting surface 1014 of proximal ring 1012 against the nesting surface 1024 of the distal ring 1024. This wedging action locks the sheath 1050 between the proximal ring 1012 and the distal ring 1022, thereby resisting further distal movement of the sheath. In contrast, the sheath 1050 is freely movable proximally because the sheath motion unseats the proximal ring 1012 from the distal ring 1024. In the illustrated embodiment, a gripping element 1052 is disposed at a proximal end of the sheath 1050, which improves a user's grip when applying traction or tension to the sheath 1050.

Figure 11A:
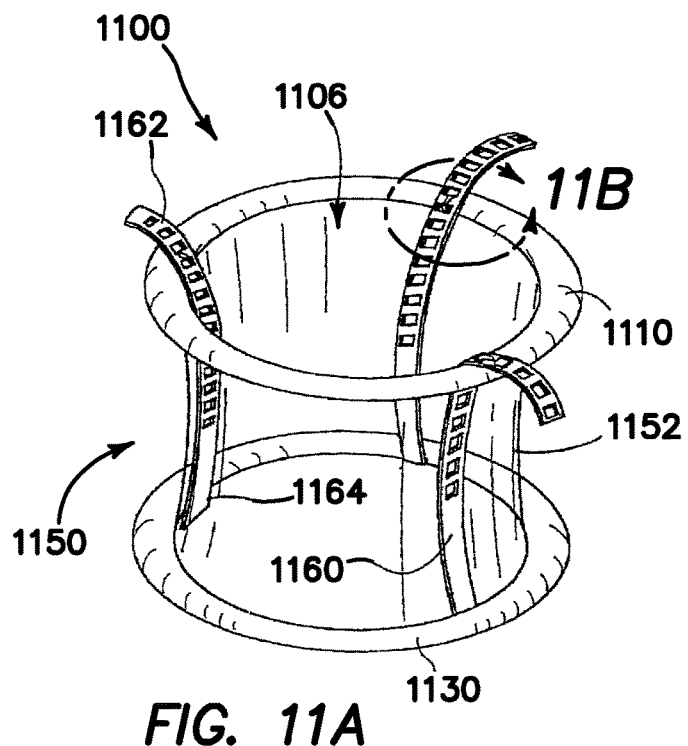
FIG. 11A is a perspective view and FIG. 11B is a detailed view of another embodiment of a retractor.
Figure 11B:
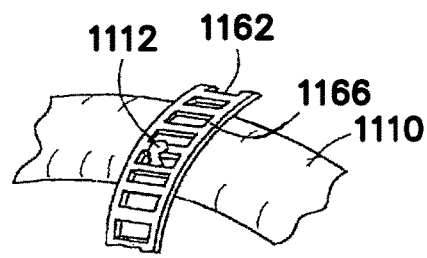

FIG. 11A is a perspective view of another embodiment of a retractor 1100, generally similar to the embodiments described above, comprising an outer ring 1110, an inner ring 1130, and a sheath 1150. In the illustrated embodiment, the sheath 1150 comprises a tubular membrane 1152 extending between the outer ring 1110 and the inner ring 1130, and a plurality of elongate bands 1160, each comprising a proximal end 1162 and a distal end 1164. The distal end 1162 of the band 1160 is secured to the distal ring 1130. The proximal end 1162 comprises a ladder-like section comprising a plurality of rungs defining opening 1166 (FIG. 11B) therebetween. The proximal ends 1162 extend through an access channel 1106 and through the outer ring 1110. As shown in FIG. 11B, which is a detail view of the outer ring 1110 and proximal end 1162 of a band 1160, the outer ring 1110 further comprises a plurality of fasteners or hooks 1112 dimensioned to engage the openings 1166 in the proximal end 1162 of the band 1160, thereby maintaining a desired tension or retraction force between the outer ring 1110 and inner ring 1130. Some embodiments of the outer ring 1110 comprise a greater number of hooks 1112 than the number of bands 1160, which provides greater flexibility in engaging each band 1160 to the outer ring 1110.

Figure 12A:
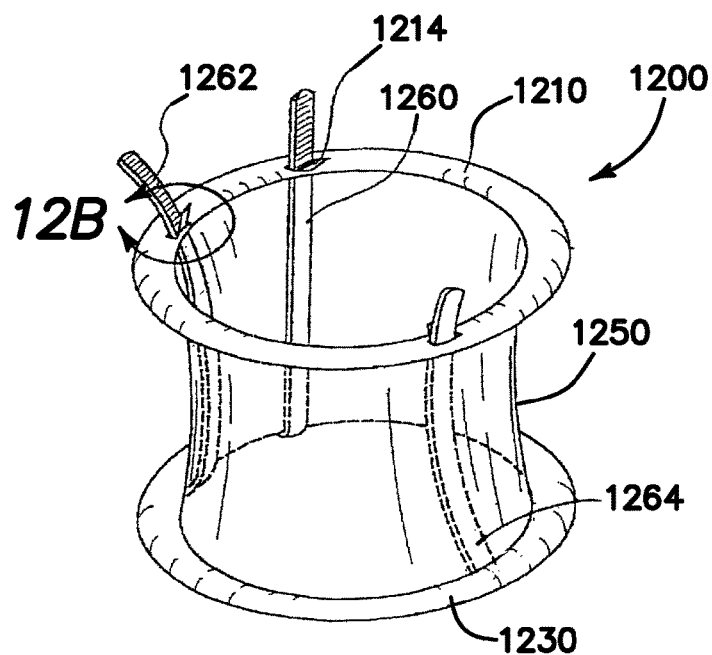
FIG. 12A is a perspective view and FIG. 12B is a detailed view of another embodiment of a retractor.
Figure 12B:
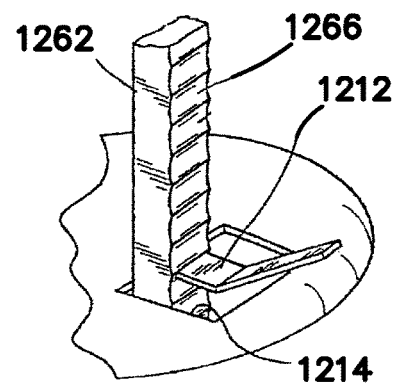

FIG. 12A is a perspective view of an embodiment of a retractor 1200 generally similar to the embodiments described above, and in particular, to the embodiment illustrated in FIGS. 11A and 11B. The retractor 1200 comprises an outer ring 1210, an inner ring 1230, and a sheath 1250, which in the illustrated embodiment, comprises a flexible membrane 1252 and a plurality of proximally extending bands 1260. A distal end 1264 of each band 1260 is secured to the distal ring 1230. A proximal end 1262 of each band 1260 extends through an opening 1214 through the outer ring 1210. As best seen in the detail view in FIG. 12B, the proximal end 1262 of the band 1260 comprises a plurality of transverse grooves 1266 which define a ratcheting surface. The outer ring 1210 comprises a pawl 1212 juxtaposed with the opening 1214. The pawl 1212 engages the grooves 1266 of the ratcheting surface. The illustrated embodiment of the pawl 1212 is also disengageable from the grooves 1266. Embodiments of the ratcheting surface and pawl 1212 are similar to corresponding elements in cable ties and zip ties. The grooves 1266 and pawl 1212 in the engaged position maintain a desired position of the band 1260, and consequently, the relative positions of the outer ring 1210 and the inner ring 1230. Hence, the mechanism permits a user to adjust and maintain the relative positions of the outer ring 1210 and the inner ring 1230, and consequently, a desired tension in the bands 1260 in retracting tissue.

Those skilled in the art will understand that similar principles are applicable to similar embodiments, for example, in which the bands comprise a plurality of enlarged or bead-like portions that engage suitably dimensioned notches in an outer ring, or in which bands and the outer ring comprise complementary hook-and-loop fasteners. In other embodiments, the bands are laces that alternately pass through openings in the outer ring and inner ring and are lockable, for example, by tying together, tying off, clamps, clips, wedges, and the like.

In an embodiment illustrated in a top cross section in FIG. 14, the inner ring 1430 has an adjustable diameter. In the illustrated embodiment, the inner ring 1430 comprises an elongate, tubular body 1432 defining a lumen 1434, wherein the body 1432 comprises a first end 1436, a second end 1438, and an opening 1440 into the lumen 1434 at the first end 1436. An elongate shaft 1442 extends from the second end 1438 of the body 1432. In the illustrated embodiment, cross sections of the lumen 1434 and opening 1440 have the same dimensions. The shaft 1442 is dimensioned to be received through the opening 1440 and into the lumen 1434, thereby defining a ring. Telescoping the shaft 1442 in or out of the body 1432 adjusts the diameter of the inner ring 1430.

In the embodiment of the inner ring 1530 illustrated in cross section in FIG. 15, the body 1432 is C-shaped, defining a channel 1534 into which a suitably dimensioned shaft 1542 is received.

In some embodiments of the above inner rings, the shaft is selectively lockable in the body, for example, using a ratchet and pawl, compressing the opening and/or lumen/channel, threads, locknuts, lock rings, friction, and the like. In the embodiment illustrated in FIG. 14, a top view of the inner ring 1430 is generally circular. In other embodiments, the inner ring has another shape as described above. Other embodiments comprise a plurality of bodies and shafts. In some embodiments, the body is two-ended, that is, each end of the body is dimensioned to receive a shaft telescopically, and the shaft is also two-ended, that is, each end of the shaft is insertable into a body. Some embodiments of the outer ring are similarly adjustable.

In an embodiment illustrated in perspective in FIG. 16, the inner anchor 1630 comprises a plurality of hooks 1632 disposed around a distal end 1654 of the sheath 1650, which when inserted into tissue, anchor the distal end 1654 of the sheath 1650. In the illustrated embodiment, two hooks 1632 are combined into a single anchoring unit. Other embodiments use individual hooks 1632 in each anchoring unit, multiple hooks 1632, or a combination thereof. Embodiments of outer anchors also comprise similar hooks.

Some embodiments of the outer anchor comprise an adhesive. In these embodiments a proximal portion 152 of the sheath 150 (FIG. 1A) is simply adhered to a patient's skin, for example, using one at least one of a pressure sensitive adhesive, a UV curing adhesive, a two-part adhesive, and the like.

Figure 17A:
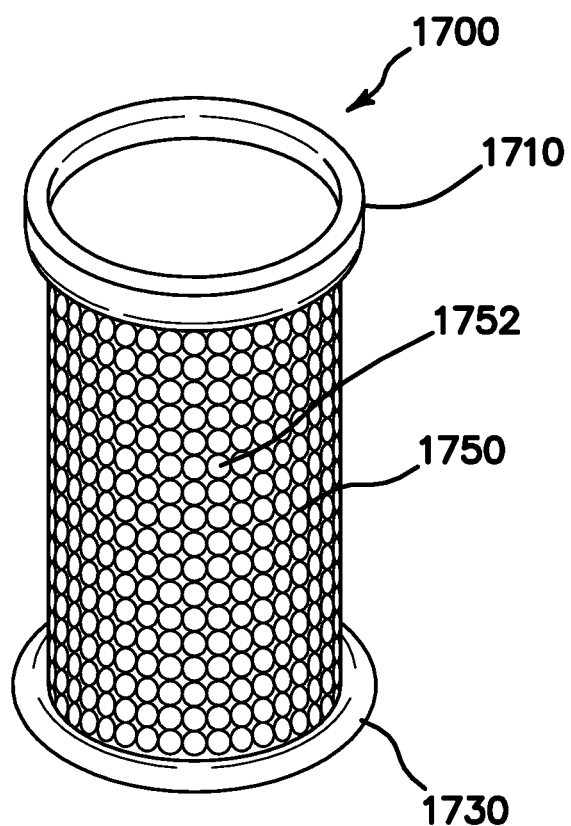
FIG. 17A is a side view of an embodiment of a retractor comprising a metal sheath.
Figure 17B:
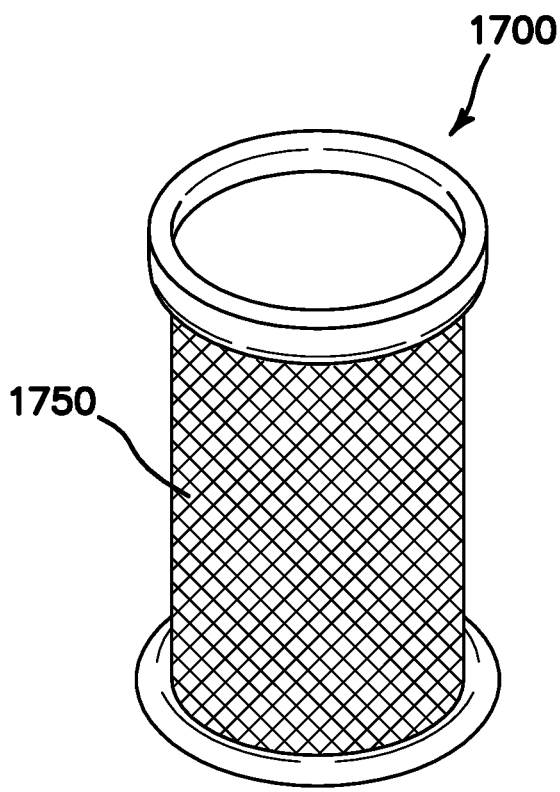
FIG. 17B is a side view of another embodiment of a retractor comprising a metal sheath.
Figure 17C:
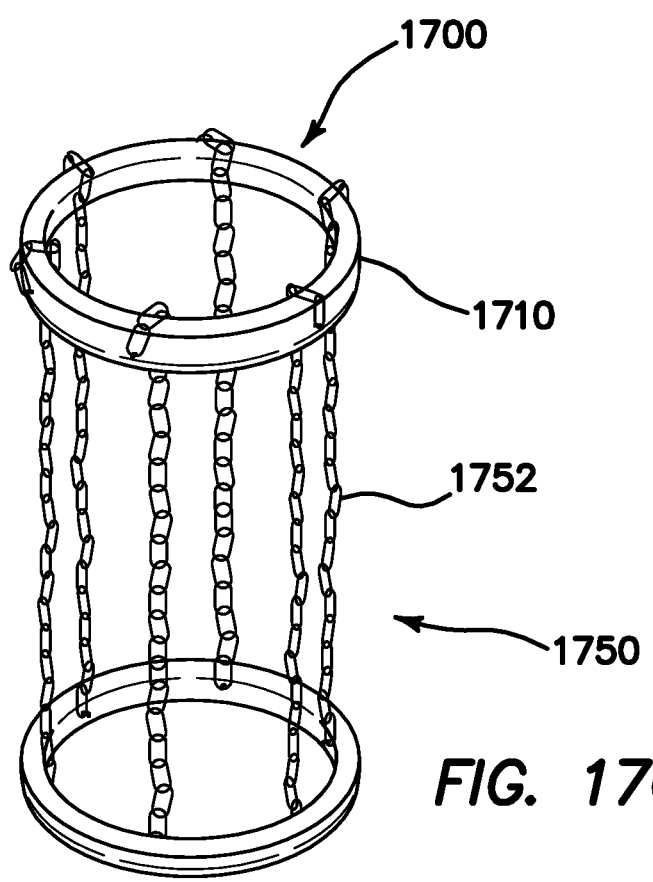
FIG. 17C is a side view of another embodiment of a retractor comprising a metal sheath.

FIGS. 17A-17C illustrate embodiments of retractors 1700 similar to the embodiments discussed above, comprising an outer ring 1710, and inner ring 1730, and a sheath 1750. In the illustrated embodiments, the sheath 750 comprises metal fibers and/or strands, for example, stainless steel, nitinol, titanium, and the like, which are autoclavable. The embodiment of the sheath 1750 illustrated in FIG. 17A comprises a mesh comprising linked loops 1752, for example, similar to chain mail. In other embodiments, the sheath 1750 comprises loops 1752 that are not interlinked, but are joined, for example, with thread or wire extending through adjacent loops longitudinally, circumferentially, diagonally, or a combination thereof. In the embodiment of the retractor 1700 illustrated in FIG. 17B, the sheath 1750 comprises braided wire. In the embodiment of the retractor 1700 illustrated in FIG. 17C, the sheath 1750 comprises a plurality of chains 1752, which are an embodiment of the bands, strips, and/or sheets discussed above. In the illustrated embodiment, the outer ring 1710 is similar to the embodiments illustrated in FIGS. 8A, 9A, and 11A. In some embodiments, the sheath 1750 further comprises a polymer film is disposed around the metal components in use, thereby protecting the incision or wound, as discussed above. In some embodiments of the sheath 1750 or portion thereof illustrated in FIGS. 17A-17C, the metal component is supplemented by or replaced with another material, for example, an engineering plastic, ceramic, a fiber reinforced composite, and the like.

Figure 13:
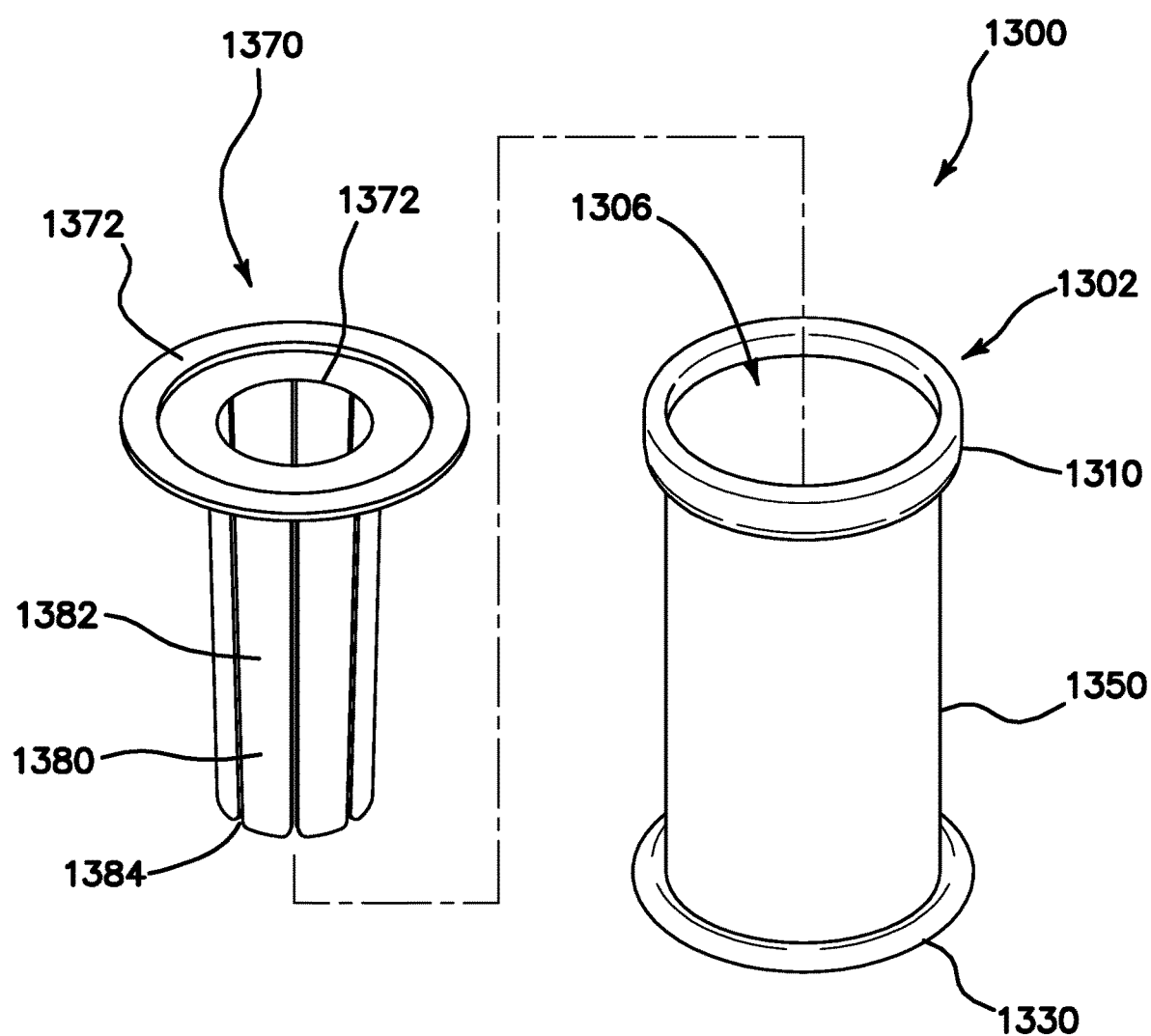
FIG. 13 is an exploded view of an embodiment of a retractor comprising a shield.

FIG. 13 is an exploded view of an embodiment of a retractor 1300, similar to the embodiments described above, comprising an outer ring 1310, an inner ring 1330, and a tubular sheath 1350, and further comprising a shield 1370. The shield 1370 is dimensioned for insertion into an access channel 1306. The shield comprises a proximal radial flange 1372 and a tubular portion 1380 extending distally from an opening 1374 in the flange 1372. In the illustrated embodiment, the tubular portion 1380 comprises a plurality of elongate fingers 1382, which define narrow gaps 1384 therebetween. In other embodiments, the tubular portion has a different configuration, for example, overlapping fingers, a tube, and the like. In the illustrated embodiment, the fingers 1382 converge. In other embodiments, the fingers do not converge, for example, are generally parallel, or diverge. In some embodiments, distal ends of the fingers 1382 diverge, thereby defining a funnel that directs instruments on withdrawal.

The flange 1372 is dimensioned to be supported either by the outer ring 1302, or in the illustrated embodiment, by tissue (skin) around an incision or opening. The opening 1374 is dimensioned to receive the largest instrument contemplated in a procedure. The flange 1372 also a portion of the sheath 1350 on which it is disposed and the underlying tissue. In the illustrated embodiment, the flange 1372 also defines a funnel for instrument insertion into the tubular portion 1380.

The shield 1370 is manufactured as a single assembly or as multiple components that are assembled into the final product. The illustrated embodiment of the shield 1370 comprises flexible or semi-rigid fingers 1382. The flange 1372 is rigid, semi-rigid, or flexible. The shield 1370 suitably comprises materials similar to those described above as suitable for the sheath. In some embodiments, the shield 1370 comprises a polymer. In some embodiments, the inner surfaces of the tubular portion 1380 are smooth.

In use, the retractor 1300 is used to retract an incision or opening as described below. The shield 1370 is then inserted into the access channel 1306 through the proximal end 1302 of the retractor 1300. The shield 1370 provides additional protection to the sheath 1350, and consequently, the retracted tissue. The shield 1370 may be removed where additional space is required for a procedure, or where the procedure presents reduced risk of tissue injury or trauma.

A method for retracting a body wall is described with reference to the embodiment of the retractor 100 illustrated in FIGS. 1A and 1B, although the method is applicable to any of the embodiments described herein.

The inner anchor or inner ring 130 is inserted though an incision, wound, or opening in the body wall. In some embodiments, inserting the inner ring 130 is facilitated by folding or collapsing the inner ring 130 prior to insertion. After insertion, the inner ring 130 is then unfolded, expanded, or deployed in the tissue in interior of the body, as described above. On completing this step, the inner ring 130 is disposed within the body, the sheath 150 extends out of the incision, and the outer anchor or outer ring 150 is disposed outside the body.

The distal end 152 of the sheath 150 is then pulled towards the user, thereby tensioning the sheath 150. The outer anchor 110 is then deployed. In the illustrated embodiment, deploying the outer anchor comprises rotating the outer ring 110 around the annular axis, thereby rolling the sheath 150 therearound, and shortening the length of the sheath 150 between the inner ring 130 and the outer ring 110. As discussed above, the outer ring 110 is rotatable in two directions: rolling-in or inversion, and rolling-out or eversion. Either rotational direction effectively rolls the sheath 150 therearound. As discussed above, in some embodiments, one direction is preferred over the other. On continued rolling, the outer ring 110 contacts the outer surface of the body wall, while the inner ring 130 contacts the inner surface of the body wall. Continued rolling of the outer ring 110 creates a desired tension on the sheath 150, thereby retracting the incision. Rolling the outer ring 110 is discontinued at a desired degree of retraction.

Also as discussed above, rotating the outer ring 110 around the annular axis occurs in discrete steps or increments. In the illustrated embodiment, the outer ring 110 comprises equilibrium or detent positions 180° apart. In these equilibrium or detent positions, the outer ring 110 resists rotation around the annular axis. Consequently, the outer ring 110 resists unrolling under the retracting tension of the sheath 150.

When unretracting or releasing the retractor, the sheath 150 is unrolled from the outer ring 110 by reversing the rolling direction of outer ring 110, thereby releasing the tension in the sheath 150. The inner ring 130 is then removed from the body cavity. As discussed above, in some embodiments, the inner ring 130 is folded or collapsed within the body cavity, thereby facilitating removal. As discussed above, in some embodiments, removing the inner ring 130 comprises pulling a tether secured thereto.

While certain embodiments have been particularly shown and described with reference to exemplary embodiments thereof, it will be understood by those of ordinary skill in the art that various changes in form and details may be made therein without departing from the spirit and scope thereof as defined by the following claims

What is claimed is:
1. A tissue retractor comprising:
a longitudinal axis defining an instrument access channel extending from a proximal end to a distal end;
an outer ring;
an inner ring that comprises an elongate tubular body that defines a lumen having a C-shape, wherein a diameter of the inner ring is adjustable, and wherein the elongate tubular body comprises:
an opening into the lumen at a first end of the elongate tubular body, and
an elongate shaft that extends from a second closed end of the elongate tubular body, the elongate shaft adapted to be received through the opening at the first end into the lumen thereby defining a ring; and a flexible sheath extending between the outer ring and the inner ring, wherein the instrument access channel extends through the outer ring, the inner ring, and the sheath;

wherein the lumen having the C-shape defined by the elongate tubular body extends along only a portion of the elongate tubular body, extending lengthwise from the first end of the elongate tubular body up to the second closed end of the elongate tubular body;

wherein the elongate shaft extends lengthwise from the second closed end of the elongate tubular body and along a portion of the elongate tubular body devoid of the lumen, the elongate shaft having an overall length greater than an overall length of the lumen, and wherein the elongate shaft has an H-shaped cross-section, the elongate shaft having an inner portion arranged to be received by the lumen, an outer portion arranged to be disposed outside of the lumen and a middle portion connecting the inner and outer portions of the H-shaped elongate shaft; and wherein an overall width of the elongate tubular body having only the elongate shaft is smaller than an overall width of the elongate tubular body with the lumen.

2. The tissue retractor of claim 1, wherein the outer ring is radially flat thereby providing the inner ring with a washer-like shape.

3. The tissue retractor of claim 1, wherein a thickness of a radial cross-section at an inner circumference of the outer ring is greater than a thickness of the radial cross-section at an outer circumference of the outer ring.

4. The tissue retractor of claim 1, wherein the inner ring comprises a single piece.

5. The tissue retractor of claim 1, further comprising a locking means that locks the elongate shaft in the lumen of the elongate tubular body to thereby fix the diameter of the inner ring.

6. The tissue retractor of claim 1, further comprising a locking means that locks the elongate shaft in the channel of the elongate tubular body to thereby fix the diameter of the inner ring.

7. The tissue retractor of claim 1, wherein dimensions of the lumen and the opening at the first end of the elongate tubular body are the same.

8. The tissue retractor of claim 1, wherein the adjustments to the diameter of the inner ring are performed by corresponding movements of the elongate shaft in or out of the elongate tubular body.

9. The tissue retractor of claim 5, wherein the locking means comprises compression of the opening and/or lumen of the elongate tubular body.

* * * * *